(12) United States Patent
Datta et al.

(10) Patent No.: US 9,677,092 B2
(45) Date of Patent: *Jun. 13, 2017

(54) INTEGRATED PROCESSES FOR ANAEROBIC CONVERSION OF HYDROGEN AND CARBON OXIDES TO ALCOHOL

(71) Applicant: Synata Bio, Inc., Warrenville, IL (US)

(72) Inventors: Rathin Datta, Chicago, IL (US); Steven G. Calderone, Chicago, IL (US); Jianxin Du, Naperville, IL (US); Robert Hickey, Okemos, MI (US)

(73) Assignee: Synata Bio, Inc., Warrenville, IL (US)

( * ) Notice: Subject to any disclaimer, the term of this patent is extended or adjusted under 35 U.S.C. 154(b) by 212 days.

This patent is subject to a terminal disclaimer.

(21) Appl. No.: 14/175,905

(22) Filed: Feb. 7, 2014

(65) Prior Publication Data

US 2014/0227751 A1  Aug. 14, 2014

Related U.S. Application Data

(60) Provisional application No. 61/762,715, filed on Feb. 8, 2013.

(51) Int. Cl.
*C12P 7/04* (2006.01)
*C12P 7/08* (2006.01)
*C12P 7/16* (2006.01)
*C12P 7/06* (2006.01)

(52) U.S. Cl.
CPC ............. *C12P 7/04* (2013.01); *C12P 7/065* (2013.01); *C12P 7/08* (2013.01); *C12P 7/16* (2013.01); *Y02E 50/10* (2013.01); *Y02E 50/17* (2013.01); *Y02E 50/343* (2013.01); *Y02E 50/346* (2013.01); *Y02P 20/125* (2015.11)

(58) Field of Classification Search
None
See application file for complete search history.

(56) References Cited

U.S. PATENT DOCUMENTS

2010/0105118 A1* 4/2010 Bell .................. C01B 3/382
435/155

FOREIGN PATENT DOCUMENTS

NZ  WO2011/139163  * 11/2011 ............... C12P 7/06

* cited by examiner

*Primary Examiner* — Karen Cochrane Carlson
*Assistant Examiner* — Jennifer M. H. Tichy
(74) *Attorney, Agent, or Firm* — Cardinal Law Group

(57) ABSTRACT

Integrated processes are disclosed for the anaerobic bioconversion of syngas to alcohol.

9 Claims, 7 Drawing Sheets

INTEGRATED PROCESSES FOR ANAEROBIC CONVERSION OF HYDROGEN AND CARBON OXIDES TO ALCOHOL

CROSS REFERENCE TO RELATED APPLICATIONS

Priority is claimed to U.S. provisional application Ser. No. 61/762,715, filed on Feb. 8, 2013.

FIELD OF THE INVENTION

This invention pertains to integrated processes for anaerobic conversion of hydrogen and carbon oxides to alcohol especially ethanol, propanol and butanol.

BACKGROUND

Anaerobic fermentations of hydrogen and carbon monoxide involve the contact of the substrate gas in an aqueous fermentation menstruum with microorganisms capable of generating alcohols such as ethanol, propanol, i-butanol and n-butanol. The production of these alcohols requires significant amounts of hydrogen and carbon monoxide. For instance, the theoretical equations for the conversion of carbon monoxide and hydrogen to ethanol are:

$$6CO + 3H_2O \rightarrow C_2H_5OH + 4CO_2$$

$$6H_2 + 2CO_2 \rightarrow C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, from partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

These substrate gases are typically more expensive than equivalent heat content amounts of fossil fuels. Hence, a desire exists to use these gases efficiently to make higher value products. The financial viability of any conversion process, especially to commodity chemicals such as ethanol, will depend, in part, upon the costs of the feedstocks, conversion efficiency and operating and capital costs for generating the substrate gases; and upon the capital costs, the efficiency of conversion of the carbon monoxide and hydrogen to the sought products and the energy costs to effect the conversion of the substrate gases to the higher value products.

In a bioreactor, hydrogen and carbon oxides pass from the gas phase to being dissolved in the aqueous menstruum, and then the dissolved hydrogen and carbon oxides contact the microorganisms for bioconversion. Due to the low solubilities of carbon monoxide and, especially, hydrogen in aqueous media, mass transfer can be a factor limiting rate and conversion in the bioconversion to alcohol. Therefore challenges exist in the design of commercial scale bioreactors that provide for the sought mass transfer while still enabling a high conversion of gas substrate at capital and operating costs that enable such a facility to be commercially competitive.

From the standpoint of low capital and energy consumption, deep tank bioreactors have been proposed to provide longer contact times between the substrate gases and the aqueous fermentation menstruum with the objective of obtaining higher conversions of the substrate gases to the higher value products. In deep tank bioreactors, the height of the aqueous menstruum is a significant determinant of the contact time for the mass transfer and bioconversion to occur. On a commercial scale, deep tank bioreactors have a depth of at least about 10, preferably at least about 15, meters.

One type of deep tank bioreactor is a stirred tank bioreactor which uses a motor driven impeller to provide liquid flow in the bioreactor and distribute the gases in the aqueous menstruum. The stirring may also facilitate increasing the contact time between the gases and the aqueous menstruum. Due to the scale, low stirring rates are typically used in deep tank bioreactors. Another type of deep tank bioreactor is a bubble column bioreactor wherein the substrate gases are introduced at the bottom of the vessel and bubble through the aqueous menstruum. Advantageously, commercial-scale bubble column bioreactors are relatively simple in design and construction and require relatively little energy to operate. Achieving liquid mixing in a deep tank bubble column can be problematic. Mechanically pumping aqueous menstruum may facilitate liquid flow. As discussed herein, the use of smaller bubbles may form lower density dispersions that facilitate mixing. Moreover, smaller bubbles favor the mass transfer of hydrogen and carbon oxides from the gas phase to liquid phase. A third type of deep tank bioreactor uses one or more, gas-lift riser sections to facilitate liquid flow and mixing. Typically, gas is introduced at the bottom of a riser section and due to a lower density, the aqueous menstruum flows upwardly. At the top of the riser section, the liquid phase passes to a down flow section for return to the bottom of the riser section.

The off gases from bioreactors contain substrate that was not bioconverted and diluents such as methane and nitrogen. Although off gases can be recycled to the bioreactor or passed to another bioreactor, challenges can exist. For instance, the substrate gases may contain diluents that if recycled to a bioreactor, can build-up and reduce the partial pressure, thus reducing the driving forces for mass transfer of hydrogen and carbon monoxide to the aqueous menstruum. Moreover, the off gas from a deep tank bioreactor would need to be compressed for recycle or for passage to a sequential bioreactor. A sequential bioreactor represents additional capital and operating costs, and since the concentration of hydrogen and carbon monoxide in the off gas from the firstbioreactor is reduced due to the anaerobic bioconversion, the incremental conversion efficiencies achieved may not be economically justifiable.

Bell in United States published patent application No. 20100105118 discloses an integrated process for making alcohols which is said to provide high bioconversions of carbon monoxide in fermentations in the absence of oxygen. Bell notes at paragraph 0013 that in theory, carbon dioxide may be used as a reactant for the production of higher alcohols such as ethanol. However, he states that in practice the fermentation route to higher alcohols tends to be a net producer of carbon dioxide. In his disclosed process, the gas from the bioreactor which contains carbon dioxide is fed to a reaction section of a steam reformer. The reformer is either operated dry or with a mole ratio of water to carbon dioxide of less than 5:1. Bell states in paragraph 0025:

" . . . the integrated process of the present invention operates with a hydrogen excess and efficiently converts the carbon dioxide in the feed to the reforming process to carbon monoxide, and actually results in a lower process inventory of carbon dioxide."

Bell confirms the carbon dioxide net make of his process and the low conversion of hydrogen in the examples. In Example 1, 107 kmoles per hour of carbon dioxide are fed to the bioreactor and 194 kmoles of carbon dioxide are contained in the off gas from the bioreactor. Hydrogen is fed to the bioreactor at a rate of 318 kmoles per hour, and 231 kmoles per hour of hydrogen are contained in the off gas for a hydrogen conversion of about 28 percent. Similarly in Example 2, the feed to the bioreactor contains 25 kmole per hour of carbon dioxide, and 117 kmole per hour of carbon dioxide is contained in the off gas. Hydrogen is fed to the bioreactor at a rate of 298 kmole per hour with 206 kmole per hour of hydrogen passing to the off gas for a hydrogen conversion of about 31 percent. Bell subjects the off gas to a membrane separation unit operation to remove hydrogen to reduce the amount of hydrogen being passed back to the reformer. This hydrogen is fed to the hot box of the reformer as a portion of the fuel. See paragraphs 0074 and 0075.

Although Bell may have reduced carbon dioxide emissions as compared to the use of autothermal reforming or traditional steam reforming, the low conversion of hydrogen detracts from the commercial viability of the disclosed process.

Processes are therefore sought that can provide very high conversions of hydrogen and carbon monoxide in commercial-scale, continuous operations to alcohol.

SUMMARY

By this invention continuous processes are provided for the anaerobic conversion of hydrogen and carbon oxides to higher alcohols, especially ethanol, propanol and butanol, in which the anaerobic fermentation unit operations are integrated with unit operations to provide substrate gas and thereby enhance the efficiencies of bioconversion. In particular it has been found that the combination of high conversion and a specific range of e/C ratio provides a surprising productivity to higher alcohols and facilitates the use of feed gas substrates comprising mixtures of non-renewable and renewable gas sources to provide higher alcohols with renewable carbon component.

First Broad Aspect of the Invention—Syngas Adjustment to Obtain Certain $e^-/C$

It has been found that the efficiency of hydrogen bioconversion in anaerobic processes depends not only on the presence of carbon dioxide in the aqueous fermentation menstruum but also the ratio of electrons to carbon atoms. The processes of this aspect of the invention enable the use of advantageous syngas sources yet obtain enhanced conversion of the syngas by adjustment of the composition of the syngas by the addition of an additional gas. The adjustment in the composition by the addition of at least one other gas is particularly attractive because all hydrogen and carbon oxides values in the feed gases are available for the bioconversion. Moreover, compositional adjustments can be readily implemented on virtually a real time basis by the blend ratio. Hence, in the event that a unit operation generating syngas has an upset or other process change affecting syngas composition, the electron to carbon (e/C) ratio can be adjusted quickly to avoid undue loss of syngas values due to the use of less desirable electron to carbon atom ratios.

In this aspect, continuous processes are provided for the anaerobic bioconversion of a gas substrate comprising carbon monoxide, hydrogen and carbon dioxide in an aqueous menstruum containing microorganisms suitable for converting said substrate to alcohol that comprise continuously contacting said gas substrate with said aqueous menstruum to bioconvert the gas substrate to alcohol and providing an alcohol-containing menstruum and a depleted gas phase; continuously withdrawing the depleted gas phase from said aqueous menstruum; continuously or intermittently withdrawing a portion of said menstruum for recovery of said alcohol, said withdrawal being sufficient to maintain the alcohol in said menstruum below a concentration that unduly adversely affects the microorganisms, wherein at least 2 gases having different compositions are used as the gas substrate and may be admixed prior to contact with the aqueous menstruum or separately added to the aqueous menstruum to provide an overall, or cumulative gas substrate having a ratio of electrons to carbon atoms in the range of about 5.2:1 to 6.8:1, preferably between about 5.5:1 to 6.5:1, and most preferably between about 5.7:1 to 6.4:1.

In one set of preferred embodiments for this aspect of the invention, syngas having a high concentration of hydrogen such as syngas generated by steam reforming or coke oven gas can be used with a gas containing a high concentration of carbon oxides, especially a high concentration of carbon dioxide. Autothermal reforming can provide syngas falling within a broad range of electrons to carbon atoms and may be in, above or below the sought ratios. In some instances, the source of carbon oxides may be relatively inexpensive, especially where carbon dioxide is a substantial portion of the gas, e.g., at least 40 volume percent carbon dioxide. A particularly attractive source of carbon dioxide is from fermentations and in most cases anaerobic fermentations, e.g., fermentations of carbohydrates such as sugars or starches to produce alkanols such as ethanol, propanol, propanediol, butanol and butanediol. Typically the carbon dioxide from these fermentations is a co-product and is relatively free of components that are unduly adverse to microorganisms.

As can be seen, the use of two or more gases enables an alcohol to be produced from both fossil and renewable carbon sources thereby providing an alcohol that has a renewable component. For example, steam reforming of methane provides a high hydrogen to carbon oxides syngas. The addition of carbon dioxide from renewable sources can, if desired, result in between about 20 or 30 to 70, say about 30 to 50, percent of the carbon atoms in the alcohol being from the renewable resource.

The fermentation is conducted in a bioreactor assembly containing one or more bioreactors. Any suitable bioreactor may be used including but not limited to bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform. The bioreactors need not, but can, provide a substantially uniform aqueous menstruum composition.

Second Broad Aspect of the Invention—Alcohol with Renewable Carbon Content

Substantial reserves of natural gas exist, and techniques are being applied to recover natural gas from these reserves.

Often, however, these reserves are located remote from large population centers and thus pose transport challenges. Pipelines, which are expensive and time-consuming to construct, can be used to transport large quantities of natural gas. Although natural gas has been shipped via tankers, specialized construction is required and the presence of highly flammable, volatile gas poses safety risks which are heightened in more developed areas. Another fossil fuel having substantial reserves is coal. Many of these reserves are located remote from large population centers and include low rank sources such as subbituminous coal and lignite. Transport of coal is often by rail, and where available, ships and barges. The costs of handling solids for transport are greater than cost for handling liquids. Moreover the coal can contain sulfur, organic nitrogen, and mercury and other metals that pose environmental issues at the location of use as a fuel.

Accordingly, proposals have been made to convert natural gas and coal to liquids that are more capable of being transported with less risk. These proposals include removal of environmentally deleterious components in generating the liquid. Such proposals include converting the fossil fuel to syngas and then to a liquid product. One such proposal is the Fischer-Tropsch process that requires substantial capital and operating expense. Recently numerous proposals have been made to bioconvert syngas to alcohol, especially ethanol. Bioconversion of syngas to alcohol has also been proposed for various industrial waste gases such as steel mill gas.

Alcohol has value as a fuel or intermediate for chemical production. Governmental and private interests have placed a premium on sourcing fuels and chemical intermediates from renewable sources. Accordingly, in the United States, a substantial corn ethanol industry has matured, and efforts are being undertaken to generate ethanol from cellulosic sources. The volumes of fuels and chemical intermediates anticipated to be required in the future can result in the deployment of agrarian land to feedstock production in contrast to the production of food. Therefore it is likely that the costs to procure cellulosic materials and crops may become significantly greater than the cost to procure fossil fuels or industrial waste containing hydrogen and carbon oxides.

Some processes for producing fuels or chemical intermediates from renewable sources generate renewable carbon-containing co-products that are not useful as fuels or chemical intermediates. For instance, yeast fermentations of carbohydrate result in about one molecule of carbon dioxide being generated for each molecule of ethanol produced. Other processes such as the gasification or partial oxidation of renewable carbon feedstock result in a syngas containing more carbon dioxide than can be converted to fuel or chemical intermediates through anaerobic bioconversion.

Carbon dioxide is also generated from various waste product disposal processes. Sources of renewable carbon, for instance, are incinerated for disposal and result in the generation of carbon dioxide. Renewable carbon-containing waste, such as municipal waste and agricultural waste are subjected to anaerobic biodegradation, e.g., in landfills and anaerobic digesters, to produce biogas which contains methane and carbon dioxide.

By combining in a bioreactor assembly syngas from non-renewable carbon source with renewable carbon containing gas, substrate can be bioconverted with high efficiency to alcohol that has a renewable carbon component. In part, by providing to the bioreactor assembly an overall, or cumulative, gas substrate having an electron to carbon atom ratio between about 5.2:1 to 6.8:1, preferably between about 5.5:1 to 6.5:1, and most preferably between about 5.7:1 to 6.4:1, certain anaerobic bioconversion processes can provide for a high conversion of hydrogen and carbon oxides, e.g., preferably in excess of at least about 85, more preferably in excess of at least about 90 and most preferably in excess of at least 95, mole percent of the hydrogen and carbon oxides. These high conversion efficiencies can be obtained using deep tank bioreactors including commercial scale, bubble column bioreactors, stirred tank and bioreactors having gas-lift riser(s) of the type discussed above as well as other types of bioreactors including stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform.

Depending upon the composition of the syngas from the non-renewable carbon source and the composition of the renewable carbon-containing gas, an alcohol can be provided that contains between about 20 and 70, say between, 30 and 50, percent of the carbon from a renewable carbon source. Where the syngas from the non-renewable carbon source contains significant amounts of hydrogen, such as coke oven gas and gas from the steam reforming of natural gas, the alcohol typically has a greater renewable carbon content. Similarly, where the renewable carbon-containing gas contains a high content of carbon dioxide, especially carbon dioxide and methane, the alcohol typically has a greater renewable carbon content. Examples of these renewable carbon-containing gases include, but are not limited to, carbon dioxide from an ethanol plant and biogas, e.g., from a landfill or anaerobic digester. In some of these instances, the greater renewable content of the alcohol has between about 30 and 60 percent of the carbon from renewable carbon.

Third Broad Aspect of the Invention—Capture of Methane and $CO_2$ Values from Biogas A particularly attractive source of carbon values for the anaerobic bioconversion of syngas to an alcohol is biogas which contains substantial amounts of both carbon dioxide and methane. Both of the carbon dioxide and the methane are from renewable resources and thus could provide alcohol with a renewable carbon component.

The processes of this aspect of the invention use a combination of steam reforming to provide a syngas having a high hydrogen content such that it can be combined with biogas containing a substantial portion of carbon dioxide and yet provide a combined gas in which during anaerobic bioconversion each of hydrogen, carbon monoxide and carbon dioxide are converted to an alcohol such that the depleted gas phase from the anaerobic bioconversion contains a reduced concentration of carbon dioxide. The depleted gas phase can therefore be used in the steam reforming either or both as a fuel to the hotbox of the steam reformer or as a portion of the feed to the steam reformer. In the latter case, because the concentration of carbon dioxide is reduced, an attractive ratio of hydrogen to carbon oxides can be obtained in the produced syngas to maximize the amount of biogas that can be incorporated in the feed to the anaerobic bioconversion. It is also possible to separate carbon dioxide from the methane in the depleted gas phase and send the carbon dioxide to the fermenter and a resulting rich methane stream to the hot box.

In some instances, the biogas may contain nutrients for the microorganisms such as sulfur compounds and ammonia or other nitrogen-containing compounds. Additionally, the aqueous menstruum may remove components such as silica, silicates and siloxanes, that could be disadvantageous if the substrate depleted gas phase were to be directly fed to the steam reformer, but which are not unduly adverse to the microorganisms.

This aspect of the invention broadly relates to continuous processes for the anaerobic bioconversion of a gas substrate comprising carbon monoxide, hydrogen and carbon dioxide in an aqueous menstruum containing microorganisms suitable for converting said substrate to an alcohol that comprises:

a. steam reforming hydrocarbonaceous feedstock to provide a syngas having an electron to carbon ratio greater than about 7:1, preferably greater than about 7.5:1, said steam reforming being performed in a steam reformer having at least one gas reforming section and at least one hotbox section;

b. continuously introducing separately or in admixture into a bioreactor assembly, said syngas and biogas, said biogas comprising at least about 20 or preferably at least 25, and sometimes at least 40, mole percent carbon dioxide and preferably at least about 40 mole percent methane, said biogas having an electron to carbon ratio less than about 0.1:1 to provide a cumulative gas substrate having an electron to carbon ratio in the range of about 5.2:1 to 6.8:1, preferably between about 5.7:1 to 6.4:1, and most preferably between about 5.8:1 to 6.3:1;

c. continuously contacting said syngas and said biogas with said aqueous menstruum to bioconvert the gas substrate to an alcohol and thereby producing an alcohol-containing menstruum and a substrate depleted gas phase, said contacting being in a bioreactor assembly containing said menstruum, said bioreactor assembly having at least one gas inlet and at least one gas outlet, and at least one bioreactor in the bioreactor assembly is characterized as having a substantially uniform liquid phase and a substantially non-uniform substrate concentration between the gas inlet and the gas outlet portion;

d. continuously withdrawing the substrate depleted gas phase from said aqueous menstruum, said depleted gas phase having a lower mole ratio of carbon dioxide to methane than that of the combined gas;

e. passing at least a portion of the depleted gas phase to the steam reformer of step (a); and f. continuously or intermittently withdrawing a portion of said menstruum for recovery of said alcohol, said withdrawal being sufficient to maintain the alcohol in said menstruum below a concentration that unduly adversely affects the microorganisms.

Especially where at least a portion of the substrate depleted gas phase is fed to the steam reformer for reformation, the partial pressure of carbon dioxide in the substrate depleted gas phase is less than about 20 or 25 kPa, and most preferably in the range of between about 2.5 or 3.5 and 10 kPa such that the production of hydrogen by the steam reformer is not unduly adversely affected by carbon dioxide reforming to produce carbon monoxide. Often the methane in the substrate depleted off gas is between about 20 to 90, and preferably, 50 to 90, mole percent of the substrate depleted gas phase. The preferred supplemental hydrocarbonaceous feedstock is natural gas.

Preferably the biogas is subjected to ultrafiltration to remove any entrained microorganisms prior to being introduced into the bioreactor assembly. The preferred biogas is an anaerobically derived gas.

Fourth Broad Aspect of the Invention—Use of Substrate Depleted Gas Phase in Hot Box In this broad aspect of the invention, hydrogen and carbon oxides in the gas substrate at certain electron to carbon atom ratios are highly converted in an anaerobic bioconversion to alcohol such that the substrate depleted gas phase from the anaerobic bioconversion has sufficient caloric value to offset fuel required for steam reforming to generate syngas for use in the gas substrate. The mole concentration of carbon dioxide in the substrate depleted gas phase is below about 20 or 25 percent, and most often in the range of between about 2.5 or 3.5 to 10 percent. A substantial portion of the heating value of the depleted gas phase is from methane and residual hydrogen contained in the gas substrate, at least portion of the methane is provided by breakthrough from the steam reformer. Advantageously, where the gas substrate comprises syngas from steam reforming, the nitrogen content of the gas substrate is preferably less than about 10, more preferably less than about 2, mole percent. These lower levels of nitrogen are achievable because steam reforming requires no addition of air or oxygen enriched air to the gas that is being reformed. Since the substrate depleted gas has a high calorific value, the use of unit operations to remove carbon dioxide is not required.

This broad aspect of the invention accordingly relates to continuous processes for the anaerobic bioconversion of a gas substrate comprising carbon monoxide, hydrogen and carbon dioxide in an aqueous menstruum containing microorganisms suitable for converting said substrate to alcohol that comprise:

a. continuously introducing into a bioreactor assembly containing aqueous menstruum a gas substrate having an electron to carbon ratio greater than about 5.2:1, preferably greater than about 5.5:1;

b. continuously contacting said syngas with said aqueous menstruum to bioconvert gas substrate to alcohol and providing an alcohol-containing menstruum and a substrate depleted gas phase;

c. continuously withdrawing the substrate depleted gas phase from said aqueous menstruum;

d. passing at least an aliquot portion of the substrate depleted gas phase to the hot box section of the steam reformer; and e. continuously or intermittently withdrawing a portion of said menstruum for recovery of said alcohol, said withdrawal being sufficient to maintain the alcohol in said menstruum below a concentration that unduly adversely affects the microorganisms.

In preferred embodiments of this aspect of the invention, a bioreactor assembly contains the aqueous menstruum for the anaerobic bioconversion said bioreactor assembly having at least one inlet portion and at least one gas outlet portion and at least one bioreactor in the bioreactor assembly is characterized as having a substantially uniform aqueous menstruum and a substantially non-uniform substrate concentration between the inlet portion and the outlet portion.

Fifth Broad Aspect of the Invention—Use of Sequential Bioreactors with Carbon Monoxide Addition to the Feed of the Last Bioreactor Stage In the processes for the anaerobic bioconversion of hydrogen and carbon oxides to alcohol, the mass transfer of carbon monoxide into the aqueous menstruum is typically faster than that of hydrogen. Consequently, the gas phase containing the gas substrate disproportionately changes composition with the result that the electron to carbon atom ratio increases. By this aspect of the invention, it has been found that enhanced hydrogen conversion can be obtained by adding a carbon monoxide-containing gas between the bioreactors, or bioreactor stages, operating in gas flow sequence. The addition of the carbon monoxide-containing gas serves to lower the hydrogen to carbon atom ratio in the range of about 5.2:1 to 6.8:1. In some instances, the addition of the carbon monoxide-containing gas appears to provide a beneficial effect enhancing reaction rate and/or conversion of hydrogen beyond that expected from an adjustment of the hydrogen to carbon atom ratio.

This broad aspect of the invention pertains to continuous processes for the anaerobic bioconversion of a gas substrate comprising carbon monoxide, hydrogen and carbon dioxide in an aqueous menstruum containing microorganisms suitable for converting said substrate to alcohol comprising continuously introducing said gas substrate into a bioreactor assembly containing said aqueous menstruum to bioconvert gas substrate to the alcohol and providing an alcohol-containing menstruum and a depleted gas phase; continuously withdrawing depleted gas phase from said aqueous menstruum; continuously or intermittently withdrawing a portion of said menstruum for recovery of said alcohol, said withdrawal being sufficient to maintain the alcohol in said menstruum below a concentration that unduly adversely affects the microorganisms, wherein:

a. the gas substrate as introduced into the bioreactor assembly has a ratio of electrons to carbon atoms in the range of about 5.2:1 to 6.8:1;
b. the bioreactor assembly comprises at least two bioreactor stages in gas flow sequence wherein at least the last bioreactor stage in gas flow sequence is characterized as having a substantially uniform aqueous menstruum and a substantially non-uniform composition of the gas bubbles between the inlet portion and the outlet portion; and
c. a carbon monoxide-containing gas having a ratio of electrons to carbon atoms less than about 6.5:1 is introduced into the last bioreactor stage in an amount sufficient to provide a ratio of electrons to carbon atoms in the admixed gases in the range of about 5.2 to 7.5:1, preferably in the range of about 5.5:1 to 6.8:1.

In preferred embodiments of this aspect of the invention, a bioreactor assembly contains the aqueous menstruum for the anaerobic bioconversion said bioreactor assembly having at least one inlet portion and at least one gas outlet portion and at least one bioreactor in the bioreactor assembly is characterized as having a substantially uniform aqueous menstruum and a substantially non-uniform composition of the gas bubbles between the inlet portion and the outlet portion. Any suitable bioreactor may be used including but not limited to bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors. A plurality of bioreactors in sequential gas flow may be desired where the substrate concentration in a bioreactor tends to be relatively uniform. The bioreactors need not, but can, provide a substantially uniform aqueous menstruum composition. Deep tank bioreactors, especially deep tank bubble column bioreactors, and membrane bioreactors, used exclusively or in combination with other bioreactors are preferred.

In some instances, the mole ratio of hydrogen to carbon monoxide in the gas passing to the last bioreactor, or bioreactor stage, is less than about 6.5:1, and if such a source of carbon monoxide is available, less than about 5:1, say, in the range of about 2:1 to 4:1.

Sixth Broad Aspect of the Invention—Integrated Carbohydrate to Alcohol and Anaerobic Syngas Bioconversion Process This aspect of the invention relates to processes for making alcohol from a combination of non-renewable and renewable feed gases. Using carbon dioxide gas from renewable carbohydrate sources is a particularly desirable source of renewable carbon atoms to adjust the electron to carbon atom ratio of a non-renewable syngas having a high electron to carbon ratio such as syngas from steam reforming of natural gas. The ability to use these non-renewable and renewable feed gas sources results from the discovery that the combination of high conversion and a specific range of e/C ratio provides a surprising productivity to higher alcohols.

In its broadest scope this aspect of the invention pertains to the use of carbon dioxide gas, which is based upon renewable and non-renewable carbon, to provide a gas substrate for anaerobic bioconversion that has an e/C ratio of between about 5.2:1 to 6.8:1 and preferably 5.7:1 to 6.4:1 and more preferably 5.8:1 to 6.3:1, and sometimes between about 5.8:1 and 6.0:1. In accordance with the more preferred embodiments, additional integrations exist to enhance further the economics of each of these processes.

Thus in this broad aspect of the invention a non-renewable, methane rich gas feed passes to a steam reformer to produce a non-renewable substrate, a portion of which, is continuously introduced into a bioreactor assembly containing an aqueous menstruum and renewable carbon dioxide is introduced into the bioreactor assembly to bioconvert the non-renewable and renewable gas substrate to alcohol and an alcohol-containing menstruum and a depleted gas phase are produced thereby, wherein in the process:

a. the steam reformer produces a gas with and e/C ratio of greater than 7.0:1 and more preferably 7.5:1 with entirely non-renewable carbon content;
b. gas from the reformer is introduced into a renewable $CO_2$-containing gas to produce a mixed gas with an e/C ratio of 5.7:1 to 6.4 to:1 which is then fed to the aqueous menstruum of the bioreactor assembly;
c. continuously withdraws depleted gas phase from said aqueous menstruum;
d. continuously or intermittently withdraws a portion of said menstruum for recovery of said alcohol; and,
e. separates the withdrawn portion of said menstruum by distillation to provide alcohol and an aqueous menstruum.

In many instances the renewable $CO_2$-containing gas has an e/C ratio of less than 2.5:1, preferably less than 0.1:1. In some applications of the above described process, the non-renewable and renewable substrates are combined to produce an e/C ratio of a combined substrate having an e/C in a range an e/C ratio of 5.8:1 to 6.0:1; the reformer is operated primarily with steam and the feed to the reformer preferably consists essentially of methane and steam; the non-renewable substrate and the renewable substrate enter a bioreactor of the bioreactor assembly independently; continuously or intermittently withdrawing a portion of said menstruum for recovery of said alcohol, said withdrawal being sufficient to maintain the alcohol in said menstruum below a concentration that unduly adversely affects the microorganisms.

As stated above, carbon dioxide gas from carbohydrate fermentation sources such as sugar or starch ethanol facilities is a desirable source of renewable carbon atoms to adjust the electron to carbon atom ratio of a syngas having a high electron to carbon ratio such as syngas from steam reforming This aspect of the invention in its broadest scope pertains to the use of the carbon dioxide gas, which is based upon renewable carbon from corn as a carbohydrate source, to provide a gas substrate for anaerobic bioconversion that has an electron to carbon atom ratio of between about 5.2:1 to 6.8:1.

This broad aspect of the invention relates to integrated processes for making alcohol from carbohydrates and gas substrate comprising carbon monoxide, hydrogen and carbon dioxide comprising:
a. a carbohydrate to alcohol process comprising:
  i. bioconverting under fermentation conditions including the presence of biocatalyst a carbohydrate-containing aqueous broth to provide an alcohol-containing broth which broth contains biocatalyst and carbon dioxide gas;
  ii. removing carbon dioxide gas as a biogas from the alcohol-containing broth;
  iii. separating by distillation alcohol from said alcohol-containing broth and providing a whole stillage containing water, unconverted carbohydrates and biocatalyst;
  iv. separating the whole stillage by centrifugation to provide a thin stillage and distillers grains;
  v. evaporating water from the thin stillage to provide a concentrate containing unconverted carbohydrates, and
b. a syngas to alcohol process comprising:
  i. continuously introducing said gas substrate into a bioreactor assembly containing said aqueous menstruum to bioconvert gas substrate to alcohol and providing an alcohol-containing menstruum and a depleted gas phase;
  ii. continuously withdrawing depleted gas phase from said aqueous menstruum;
  iii. continuously or intermittently withdrawing a portion of said menstruum for recovery of said alcohol,
  iv. separating the withdrawn portion of said menstruum by distillation to provide alcohol and an aqueous stillage,
wherein at least a portion of the separated carbon dioxide from step (a)(ii) is used as a portion of the gas substrate in step (b)(i) to provide a gas substrate having an electron to carbon atom ratio of between about 5.2:1 and 6.8:1, preferably between about 5.5:1 to 6.5:1 and most preferably, 5.7:1 to 6.4:1.

Preferably the gas substrate of step (b)(i) comprises syngas derived from steam reforming or coke oven gas.

One additional integration is the use of the evaporation of step (a)(v) to treat water from the anaerobic bioconversion process. The integration of the carbohydrate ethanol process and the anaerobic bioconversion process provides for water conservation. By introducing water from the anaerobic bioconversion process into the evaporation of step (a)(v), the water is substantially sterilized and thus can be used in the ethanol process. Additionally, the evaporation serves to provide water having a reduced salt, especially sodium ion, concentration. In carbohydrate ethanol plants the microorganisms used for the fermentation are ultimately recovered as dried distillers grains which have value as animal feed. Consequently, wastewater from the ethanol plant has a significant deficiency in nitrogen to support microbial wastewater treatment. Typically ethanol plants introduce ammonia to the wastewater treatment facility to supply the necessary nitrogen content. Water containing cell debris from the anaerobic bioconversion can be provided to a wastewater treatment facility for an ethanol plant to offset, if not totally replace, ammonia as the nitrogen source for wastewater treatment.

Seventh Broad Aspect of the Invention—Latent Heat Recovery from Waste Heat Boiler Reformate Steam reformers and autothermal reformers are typically highly heat integrated to reduce the amount of energy required to generate the high temperatures required for the reforming. Usually additional heat is recovered from the syngas using a waste heat boiler which typically provides steam at a temperature of about 120° C. to 140° C. for process use. The cooled syngas is typically saturated with water and is at a pressure of between about 300 and 1500, preferably, 500 and 1000, kPa absolute. In this aspect of the invention, it has been found that additional latent heat can be recovered from the cooled syngas and effectively used, despite its low temperature, for distillation of alcohol from aqueous menstruum. Thus, the syngas can be passed to a distillation column reboiler and is often further cooled in the reboiler to a temperature of between about 100° C. and 110° C. Latent heat is transferred in the distillation reboiler and thus water will condense in the syngas and can be removed, if desired, by phase separation. In some instances at least about 25, preferably at least about 30, and often between about 40 and 60, percent of the heat required for the distillation can be obtained from this latent heat, especially where the alcohol is ethanol.

Thus this broad aspect of the invention pertains to continuous, integrated processes for the anaerobic bioconversion of a gas substrate comprising carbon monoxide, hydrogen and carbon dioxide in an aqueous menstruum containing microorganisms suitable for converting said substrate to alcohol that comprise:
a. continuously reforming hydrocarbonaceous feedstock at elevated temperature, preferably at least about 650° C., say between about 700° C. and 800° C., and pressure, preferably between about 300 and 1500, more preferably between about 500 and 1000, kPa absolute, to provide a syngas containing hydrogen, carbon monoxide, carbon dioxide and water vapor, said reforming comprising heat exchange between the syngas and the hydrocarbonaceous feedstock;
b. continuously generating steam from the syngas to provide a first cooled syngas, said first cooled syngas preferably being at a temperature between about 120° and 140° C. and saturated with water vapor;
c. continuously passing the first cooled syngas to a distillation reboiler to provide a second cooled syngas having a temperature preferably between about 100° C. and 110° C.;
d. continuously contacting said second cooled syngas with said aqueous menstruum to bioconvert gas substrate to alcohol and providing an alcohol-containing menstruum and a syngas depleted gas phase;
e. continuously withdrawing a substrate depleted gas phase from said aqueous menstruum;
f. continuously or intermittently withdrawing a portion of said menstruum for recovery of said alcohol, said withdrawal being sufficient to maintain the alcohol in said menstruum below a concentration that unduly adversely affects the microorganisms; and
g. continuously recovering alcohol from said withdrawn menstruum in a distillation column, said distillation column using heat provided by step (c).

Eighth Broad Aspect of the Invention—Operation of a Series of Membrane Bioreactors Another preferred bioreactor for the bioreactor assembly is a membrane bioreactor. There are various versions of membrane bioreactors. Without limiting the variety of possible membrane arrangements, a preferred membrane bioreactor comprises a plurality of hollow fibers that provide contact of the fermentation liquid, of the microorganism retained by the membrane, and of the substrate gas.

A general arrangement of a membrane bioreactor is disclosed in patent application publication 20080205539 and a particularly preferred arrangement of a membrane bioreactor is disclosed in U.S. Pat. No. 8,329,456 The reference discloses, details of a membrane bioreactor including flow path arrangements, fiber compositions, and sizing. As shown therein the membrane bioreactor can be arranged in many different ways. Of most interest is the function of the membrane with respect to the fermentation liquid, the gas substrate and the microorganisms.

Application 20080205539, the teachings of which are hereby incorporated by reference, shows an arrangement where the microorganisms are retained as a biofilm on the membrane in direct contact with menstruum. The biofilm may be formed on either side of the membrane. The gas substrate contacts the side of the membrane opposite the biofilm and permeates the membrane to contact the microorganisms that comprise the biofilm. The gas and the biofilm together with the menstruum may be on either side of membrane, but typically the biofilm is on the outside of the membrane to prevent plugging of the fiber lumen.

U.S. Pat. No. 8,329,456, the teachings of which are hereby incorporated by reference, shows a preferred arrangement using an asymmetric membrane that retains the microorganisms in a macropore layer located on the outside of the membrane and in direct contact with the substrate while the fermentation menstruum passes on the side of the membrane opposite the substrate and microorganisms flowing the membrane and in contact with a liquid control layer of the membrane. Permeation of the menstruum through the membrane and into contact with microorganisms in the biopores is controlled by its direct contact with a liquid control layer of the membrane.

The membrane bioreactor will typically contain one or more modules that arrange the hollow fibers. The modules commonly contain a plurality of hollow fibers arranged longitudinally with respect to the length of the fiber and in line with respect to the longitudinal axis of the vessel. The ends of the fibers are most often retained in a potting material of resin that exposes open end of the fiber for fluid flow there through. Each section of potted fibers forms a separate module.

Series flow of both gas and menstruum through individual membrane bioreactors is shown in both the application and the patent. U.S. Pat. No. 8,101,387, the teachings of which are hereby incorporated by reference, also show a method for sequencing bioreactors in serial flow. Both patents and the application show arrangements for adjusting gas flow between the bioreactors. These references also show the typical construction of the membranes into elongated modules with the hollow fibers extending along the length of modules. The substrate then enters and leaves the modules through gas distribution and gas collection chambers that communicate with the inlets and outlets of the hollow fiber lumens.

In the present invention a plurality of membrane bioreactors are used in serial gas and liquid flow from bioreactor to bioreactor. As the menstruum passes through the series of bioreactors the alcohol concentration will typically increase and reach the highest concentration in the last bioreactor. Thus, uniformity of alcohol concentration does not exist from bioreactor to bioreactor. In addition without any adjustment of the gas between bioreactors, the e/C ratio will vary through the series of bioreactors.

An essentially uniform e/C may be maintained for the assembly. Additional substrate gas or portions thereof are readily added between bioreactors or modules in the overall assembly. Furthermore, the number of additions is readily varied by adjusting the size of the modules, primarily increasing the length or the number of fibers in the modules, to increase the gas addition points between the individual membrane modules. Thus, composition gas substrate may be adjusted as desired by the addition or withdrawal of gas between the number of modules or bioreactors that are provided. The desired e/C values are in the range of about 5.2:1 to 6.8:1, preferably between about 5.5:1 to 6.5:1, and most preferably between about 5.7:1 to 6.4:1. The substrate gas, also be adjusted to keep its carbon monoxide concentration below that which unduly inhibits the productivity of the microorganisms.

Without some adjustment in its composition, the menstruum of the last bioreactor in the series will have the highest alcohol titer. The assembly may be able to operate with its highest alcohol titer in the last module of the bioreactor assembly in the liquid flow sequence of bioreactors. However, if desired the alcohol concentration may be reduced across intermediate stages of the serial bioreactors or modules by withdrawal of relatively higher alcohol menstruum and/or the addition of fresh menstruum between serial bioreactor stages and/or modules in the bioreactor assembly. Typically the alcohol will be kept below a level that unduly adversely affects the microorganism and usually below a concentration of 10 grams per liter.

Thus, the membrane bioreactor offers a great deal of flexibility for controlling the e/C ratio and the alcohol concentration as the substrate and menstruum pass serially through the bioreactor assembly. In a broad aspect, the invention pertains to continuous processes for the anaerobic bioconversion of a gas substrate comprising carbon monoxide, hydrogen and carbon dioxide in an aqueous menstruum containing microorganisms suitable for converting said substrate to alcohol that comprise:

a. continuously passing a substrate comprising carbon monoxide, hydrogen and carbon dioxide serially through a plurality of membrane modules arranged for within a bioreactor or through a plurality of bioreactors located in a bioreactor assembly for serial flow of the substrate and the menstruum through the bioreactor assembly;

b. continuously passing a menstruum through the series of membrane bioreactor modules;

c. maintaining a desired e/C in each of the modules and, if necessary to maintain the desired e/C in a module, adding at least one of carbon monoxide, carbon dioxide or hydrogen to the gas inflow of that module;

d. maintaining a desired alcohol concentration in each of the modules and, if necessary withdrawing menstruum from one or modules and/or adding menstruum to one or more modules;

e. continuously withdrawing a substrate depleted gas phase from at least one of the modules;

f. continuously or intermittently collecting a portion of said menstruum from one or more of the modules for recovery of alcohol therefrom, said withdrawal being sufficient to maintain the alcohol in said menstruum below a concentration that unduly adversely affects the microorganisms; and g. continuously recovering alcohol from the collected menstruum.

General

The gas substrate for the anaerobic bioconversion of syngas may be obtained in any convenient manner. Preferably the gas substrate being introduced into the bioreactor assembly comprises at least about 80, preferably at least about 90, mole percent of carbon monoxide, hydrogen and carbon dioxide.

Preferably, the bioreactor assembly contains the aqueous menstruum for the anaerobic bioconversion said bioreactor assembly having at least one inlet portion and at least one gas outlet portion and at least one bioreactor in the bioreactor assembly is characterized as having a substantially uniform aqueous menstruum and a substantially non-uniform composition of the gas bubbles between the inlet portion and the outlet portion. Without wishing to be limited by theory, it is believed that this type of bioreactor assembly provides for sufficient driving force for hydrogen in gas bubbles to pass into the aqueous fermentation menstruum and thus facilitates obtaining high conversion efficiencies of hydrogen. The preferred processes use a deep tank bioreactor, most preferably a bubble column bioreactor. Advantageously, the electron to carbon ratios of the gas substrate to the bioreactor assembly result in a sufficiently low concentration of carbon monoxide in the gas substrate that carbon monoxide inhibition is not a factor in the operation of a bubble column bioreactor of the depth required to provide the sought conversions.

DETAILED DISCUSSION

Definitions

Figure 1:
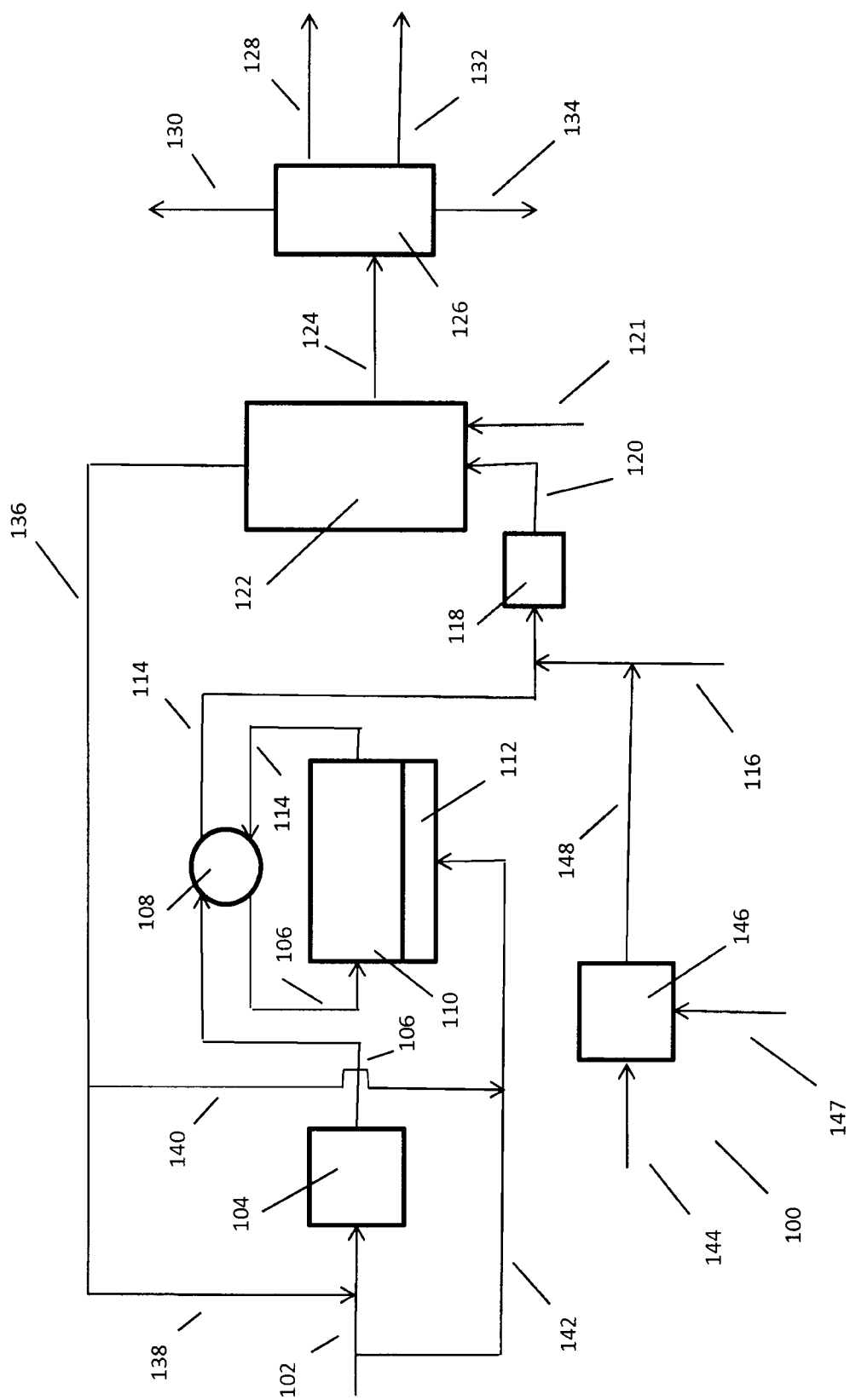
FIG. 1 is a schematic depiction of an apparatus suitable for practicing certain broad aspects of the processes of this invention.

As used herein, the following terms have the meanings set forth below unless otherwise stated or clear from the context of their use.

The use of the terms "a" and "an" is intended to include one or more of the element described.

Alcohol means one or more alkanols containing two to six carbon atoms. In some instances the alcohol is a mixture of alkanols produced by the microorganisms contained in the aqueous menstruum.

Biogas means a gas produced from a renewable source of carbon and preferably containing at least about 20 mole percent carbon dioxide.

Anaerobically derived gas means biogas produced by the anaerobic digestion or fermentation of organic matter in the absence of oxygen and primarily contains methane and carbon dioxide.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switch grass, corn (including corn stover), hemp, sorghum, sugarcane (including bagas), and the like; and waste such as garbage and municipal waste. Biomass does not include fossil fuels such as coal, natural gas, and petroleum.

The term Component Composition means the composition of a gas where both water and nitrogen have been excluded from the calculation of the concentration of the components. As used herein, unless otherwise stated, compositions of gases are on an anhydrous basis and exclude the presence of nitrogen.

Electron to carbon ratio is calculated as the quotient of the quantity of two times the sum of the concentrations of carbon monoxide and hydrogen divided by quantity of the sum of the concentrations of carbon monoxide and carbon dioxide:

$$e^-/C = 2([CO]+[H_2])/([CO]+[CO_2]).$$

The abbreviation ppm means parts per million. Unless otherwise stated or clear from the context, ppm is on a mole basis (ppm (mole)).

Carbon monoxide inhibition means that microorganisms are adversely affected by a high concentration of dissolved carbon monoxide in the aqueous menstruum resulting in a significantly reduced, e.g., reduced by at least 15 percent, conversion of carbon monoxide or hydrogen per gram of active cells per liter, all other conditions remaining the same. A high concentration of dissolved carbon monoxide means that a higher conversion of carbon monoxide or hydrogen per gram of active cells per liter occurs at a lower dissolved concentration of carbon monoxide. The inhibitory effect may occur in a localized region in the aqueous menstruum; however, the occurrence of a carbon monoxide inhibition is typically observed by assessing the specific activity rate, i.e., the mass bioconsumed per mass of active microorganism per unit time, which under steady-state conditions can be approximated by the overall conversion for the volume of aqueous menstruum in the bioreactor. The concentration of carbon monoxide dissolved in the aqueous menstruum that results in carbon monoxide inhibition varies depending upon the strain of microorganism and the fermentation conditions.

Aqueous menstruum, or aqueous fermentation menstruum, means a liquid water phase which may contain dissolved compounds including, but not limited to hydrogen, carbon monoxide, and carbon dioxide.

Intermittently means from time to time and may be at regular or irregular time intervals.

A concentration of the alcohol below that which unduly adversely affects the rate of growth of the culture of microorganisms will depend upon the type of microorganism and the alcohol. An unduly adverse effect on the growth rate means that a significant, usually at least a 20 percent, decrease in the growth rate of the microorganisms is observed in comparison to the growth rate observed in an aqueous menstruum having about 10 grams per liter alcohol therein, all other parameters being substantially the same.

Substantial uniformity in liquid phase means that composition of the liquid phase is substantially the same throughout a bioreactor. Usually the concentration of the alcohol is within about 0.2 mole percentage points in a uniform liquid phase.

Substantial non-uniformity in the gas phase means that the concentration (both in the gas bubbles and dissolved) of at least one component provided by the gas substrate changes by at least 50 percent between the point of entry of the gas into a bioreactor and the point that the gas emerges from the aqueous fermentation menstruum.

Deep tank bioreactor is a bioreactor having a depth of at least about 10 meters and can be operated to provide a substantial non-uniform substrate composition over the depth of the aqueous menstruum contained in the bioreactor. The term bubble column bioreactor as used herein refers to a deep tank bubble column bioreactor unless otherwise explicitly stated and include deep tank reactors where the gas is introduced as small bubbles to promote mixing. A commercial scale bioreactor has a capacity for aqueous menstruum of at least 1 million, and more preferably at least about 5, say, about 5 to 25 million, liters.

Stable gas-in-liquid dispersion means a mixture of gas bubbles in liquid where the bubbles predominantly flow in the same direction as the liquid currents in the bioreactor and may cause currents in the bioreactor, and the dispersion is sufficiently stable that it exists throughout the aqueous menstruum.

Syngas means a gas containing at least one of hydrogen and carbon monoxide and may, and usually does, contain carbon dioxide.

Coal gas has a typical composition of between about 3 and 8 volume percent carbon dioxide, about 20 to 35 volume percent carbon monoxide, about 12 to 25 volume percent hydrogen, and essentially the balance comprising nitrogen.

Coke oven gas has a typical composition of between about 1 and 5 volume percent carbon dioxide, about 3 and 10 volume percent carbon monoxide, about 20 and 40 volume percent methane, about 40 and 60 volume percent hydrogen with the balance being primarily nitrogen.

Anaerobic digester gas has a typical composition of between about 25 and 50 volume percent carbon dioxide and about 40 and 70 volume percent methane with small amounts of hydrogen, hydrogen sulfide, ammonia, and nitrogen.

Landfill gas has the typical composition of between about 35 and 60 volume percent carbon dioxide and about 35 and 60 volume percent methane with small amounts of carbon monoxide, hydrogen, hydrogen sulfide, oxygen, and nitrogen.

Steel mill gas has a composition of between about 30 and 85 volume percent carbon monoxide, about 10 to 40 volume percent carbon dioxide, and about 0 to 15 volume percent hydrogen. Nitrogen is generally present and may constitute up to about 30 volume percent of the steel mill gas. Other minor components are typically present.

Non-renewable gas stream means a gas derived from natural resources that takes at least a geologic age to replace once depleted and for this invention refers primarily to natural gas or methane stream derived fossil fuels.

Renewable sources or renewable carbon means a source of carbon that can be replaced in less than a millennium and in most cases in several years or less.

Natural gas means a combustible mixture of gaseous hydrocarbons from sedimentary rocks usually containing over 75% methane with minor amounts of 2-4 carbon alkanes.

Overview

The processes of this invention provide for high anaerobic bioconversion efficiencies of syngas to alcohol. Various aspects of the invention use certain electron to carbon ratios. And various aspects of the invention facilitate achieving a high conversion of syngas with the alcohol having a renewable carbon component.

Syngas Generation

The source of the syngas is not critical to a number of the broad aspects of this invention although for some broad aspects, the use of syngas derived from steam reforming is particularly attractive. Gasification, partial oxidation, and reforming (autothermal and steam) of biomass or fossil carbonaceous materials are representative processes for generating syngas. Gasification and partial oxidation processes are disclosed in copending U.S. patent application Ser. No. 13/304,902, filed on Nov. 28, 2011, hereby incorporated by reference in its entirety. Rice, et al, in "Autothermal Reforming of Natural Gas to Synthesis Gas", Reference: KBR Paper #2031, Sandia National Laboratories, April 2007, discuss autothermal reforming and conditions. Steam reforming is a widely practiced commercial unit operation. See Logdberg, et al., "Natural Gas Conversion", Haldor Topsoe publication (undated). Reforming in the presence of carbon dioxide is known as carbon dioxide reforming with the partial pressure of carbon dioxide causing a shift in the product distribution of the reforming. See, for instance, Madsen, et al, "Industrial Aspects of $CO_2$-reforming", Paper No. 28f, presented at the AIChE Spring Meeting, Houston, Tex., March 1997. Reforming is a temperature dependent equilibrium reaction, and thus the addition of hydrogen, carbon monoxide or carbon dioxide will affect the distribution of steam, hydrogen, carbon monoxide and carbon dioxide from the fresh feed although the distribution in the produced syngas will be set by the thermodynamic equilibria.

Where a source of carbon dioxide is available, steam reforming is generally preferred due to the high hydrogen concentration of the produced syngas and the relative absence of contaminants that must be removed to prevent deleterious effects on the microorganisms for the anaerobic bioconversion to alcohol. Additionally, steam reforming, being non-oxidative, provides a syngas that is relatively free of nitrogen which would be present in the syngas produced by a partial oxidation or autothermal reforming process using air or enriched air as the oxygen source. Another advantage of steam reforming is that the depleted gas phase from the bioreactors can be used as a portion of the fuel required for providing the heat for the steam reforming. By using the depleted gas phase to provide heat, an offset of fresh carbonaceous feed occurs and thereby enhances the net conversion of fresh carbonaceous feed to alcohol. The portion of the carbonaceous feed that can be offset will depend upon the volume and heating value of the depleted gas phase. Where this option is employed, frequently about 10 to 50 mass percent of the carbonaceous feed used for fuel in the hotbox of the steam reformer can be offset.

An advantage of autothermal reforming is that operating conditions can be selected to provide a syngas having the sought electron to carbon atom ratio. The electron to carbon ratio can be adjusted by operational variables for autothermal reforming. For instance, increasing the preheat temperature of the feed to the autothermal reforming enables a reduction in the amount of combustion required during the autothermal reforming to provide the sought temperature. Thus the concentration of carbon dioxide in the syngas is reduced. The steam to hydrocarbonaceous feed ratio can also be adjusted to provide the sought electron to carbon ratio with higher steam ratios increasing the electron to carbon ratio. Since the processes of this invention enable a high conversion of hydrogen to alcohol, advantageous processes can be provided where air or oxygen-enriched air is used as the oxygen source for the autothermal reforming. Although the nitrogen diluent may reduce the energy density of the substrate depleted gas phase from the bioreactor assembly and render it less useful or without utility as a gas for combustion to provide heat, e.g., for a steam boiler, high feedstock to alcohol conversions can still be achieved.

Since the unit operations to make the syngas can vary widely, it is understood that the compositions of the syngas may similarly vary widely including the presence of components other than hydrogen, carbon monoxide and carbon dioxide, which components may be inert such as nitrogen and methane or components that may have to be removed due to potential adverse effects on the microorganisms such as hydrogen cyanide. Processes for removing adverse components include those disclosed in U.S. patent application Ser. No. 13/304,902, filed on Nov. 28, 2011; Ser. No. 13/440,953, filed on Apr. 5, 2012; and Ser. No. 13/525,079, filed on Jun. 15, 2012; and U.S. Pat. No. 7,927,513 filed on Oct. 27, 2009 and U.S. Pat. No. 8,303,849, filed on Nov. 9, 2010, all hereby incorporated by reference in their entireties. Also, the relative ratios among hydrogen, carbon monoxide and carbon dioxide may vary widely. An advantage of the processes of this invention is that such variations in the relative ratios can be accommodated to provide a substrate gas to the bioreactor assembly that enables achieving a high conversion of hydrogen and carbon monoxide to alcohol.

In some instances, it may be desired to use more than one source of syngas, and it may be desired to use different types unit operations, e.g., a steam reformer and an autothermal reformer or partial oxidation unit or gasifier, to produce syngas so as to provide the desired substrate gas composition.

The Aspects of the Invention Using Syngas Adjustment

In certain of the broad aspects of the processes of this invention, the syngas composition is adjusted to provide one or more of certain electron to carbon ratios and renewable carbon in the alcohol product. Adjustment is effected by the addition of one or more of these components from another source having a different composition. As noted above, the use of two different syngas producing unit operations may be used to provide a composite syngas having the sought composition. Alternatively, a hydrogen or carbon oxides-containing gas from another process can be used for the adjustment, especially gases that contain carbon oxides from renewable sources.

Where hydrogen is required to be added, it can be procured from any suitable source. Coke oven gas is a particularly attractive source of hydrogen. Where a gas containing a high concentration of hydrogen is available, such as syngas from steam reforming, an opportunity exists to provide a renewable component to the alcohol product. Additional carbon dioxide can be added to meet the electron to carbon atom parameter desired for high conversion of hydrogen and carbon monoxide, and a significant amount of this additional carbon dioxide will be consumed in making the alcohol. Sources of the additional carbon dioxide can be derived directly or indirectly from biomass. One convenient source of relatively high purity carbon dioxide is from ethanol plants bioconverting carbohydrates to ethanol or other alkanols and diols. In some instances, between about 20 to 45 or more percent of the oxygenated organic product can be composed of carbon from renewable sources where using a methane steam reforming unit operation to produce syngas.

Another source of carbon dioxide-containing gas that can be used to adjust the composition of a syngas having a high hydrogen content is biogas such as from anaerobic digestion processes and from landfills. An advantage of the biogas is that it contains a significant amount of methane which can be used as, for instance, feedstock for a steam reforming unit operation or fuel within the process, e.g., for generating heat for distillation of the alcohol from the aqueous menstruum or for the hotbox of a steam reformer. Where the depleted gas phase from the bioreactor assembly is used as a feed for the steam reformer, up to about 70 percent of the oxygenated organic product can be composed of carbon from renewable sources.

Table I provides typical compositions of the cumulative substrate gas fed to the bioreactor assembly using syngas from steam reforming.

TABLE I

| Component | Minimum | Maximum | Preferred Minimum | Preferred Maximum |
|---|---|---|---|---|
| Carbon Monoxide, mole % | 0 | 30 | 10 | 20 |
| Hydrogen, mole % | 30 | 75 | 50 | 70 |
| Carbon Dioxide, mole % | 2.5 | 50 | 10 | 15 |
| Methane, mole % | 0.1 | 30 | 0.3 | 10 |
| Nitrogen, mole % | 0 | 10 | 0 | 5 |
| Ammonia, ppm (mole) | | | | |
| Hydrogen cyanide, ppm (mole) | 0.001 | 2 | 0.001 | 0.3 |
| Other, ppm (mole) | 20 | 10000 | 20 | 10000 |

(Excluding water)

Alcohol, Microorganisms and Fermentation Conditions:

The alcohol or alcohols produced in the processes of this invention will depend upon the microorganism used for the fermentation and the conditions of the fermentation. One or more microorganisms may be used in the fermentation menstruum to produce the sought alcohol. Bioconversions of CO and $H_2/CO_2$ to propanol, butanol, ethanol and other alcohols are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 U.S. Pat. No. 8,143, 037, filed on Mar. 19, 2010. All of these references are incorporated herein in their entirety.

Suitable microorganisms for bioconversion of syngas to alcohol generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and syngas residence time, are preferably sufficient to achieve the sought conversion efficiency of hydrogen and carbon monoxide and will vary depending upon the design of the fermentation bioreactor and its operation. The pressure may be subatmospheric, atmospheric or super atmospheric, and is usually in the range of from about 90 to 1000 KPa absolute and in some instances higher pressures may be desirable for biofilm fermentation bioreactors. As most bioreactor designs, especially for commercial scale operations, provide for a significant height of aqueous menstruum for the fermentation, the pressure will vary within the fermentation bioreactor based upon the static head.

The fermentation conditions are preferably sufficient to effect conversion of at least about 85, preferably at least about 90, percent of the hydrogen in the substrate gas fed to the bioreactor assembly to alcohol. As stated above, a combination of bubble size and duration of contact with the aqueous fermentation menstruum are necessary to achieve these high conversions. However, the ease and ability to achieve these high conversions is also dependent upon having the specified electron to carbon ratios and carbon dioxide partial pressures in the substrate depleted gas phase.

For commercial operations, the fermentation operation preferably provides a total molar conversion of hydrogen and carbon monoxide in the substrate gas feed in the range of at least about 93, preferably at least about 97, mole percent. If required to provide adequate contact time between the gas bubbles and the aqueous fermentation menstruum, more than one bioreactor may be used in gas flow series in the bioreactor assembly. The use of sequential deep bubble column bioreactors is disclosed in U.S. patent application Ser. No. 13/243,062, filed on Sep. 23, 2011, herein incorporated by reference in its entirety.

The rate of supply of the gas feed under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

Preferably the substrate gas is introduced into the bioreactor in the form of microbubbles. Often the microbubbles have diameters in the range of 0.01 to 0.5, preferably 0.02 to 0.3 millimeter. Preferably the substrate gas is injection using a motive fluid. Variations in the motive liquid flow rate can be used to modulate the microbubble size and thus modulate the rate of transfer of carbon monoxide and hydrogen to the liquid phase. Moreover, the modulation provides microbubbles that provide a stable gas-in-liquid dispersion. The injectors may be jet mixers/aerators or slot injectors. Slot injectors are preferred, one form of which is disclosed in U.S. Pat. No. 4,162,970. These injectors operate using a motive liquid. The injectors, especially slot injectors, are capable of operating over a wide range of liquid and gas flow rates and thus are capable of significant turn down in gas transfer capability. The injectors are characterized as having nozzles of at least about 1, often about 1.5 to 5, say, 2 to 4, centimeters as the cross-sectional dimension in the case of jet injectors or as the smaller cross-sectional dimension in the case of slot injectors. The bubble size generated by the injectors will be influenced by, among other factors, the rate of liquid flow through the injector and the ratio of gas phase to liquid phase passing through the injector as well as characteristics of the aqueous menstruum itself including, but not limited to its static liquid depth. See also, U.S. patent application Ser. No. 13/243,062, filed on Sep. 23, 2011. In some instances the microbubbles which form a less dense gas-liquid dispersion and any motive fluid used to generate the microbubbles, can facilitate liquid mixing in a bioreactor.

Bioreactor Assembly

The bioreactor assembly may comprise one or more bioreactors which may be, with respect to gas flow, in parallel or in series flow. The bioreactor assembly preferably contains a bioreactor that is characterized as having a substantially uniform aqueous phase composition and a substantially non-uniform substrate concentration. Where more than one bioreactor is used in gas flow series, at least the terminal bioreactor in the series has this characterization. Representative of these types of bioreactors are bubble column bioreactors, stirred tank bioreactors where the stifling rate is below that which results in a substantially uniform gas composition (liquid and gas phase) in the bioreactor, and bioreactors having gas-lift riser section or sections.

Because of economy of capital cost and operation, deep tank bioreactors are preferred. The deep tank bioreactors, in order to provide the sought contact time with the bubbles have a depth of at least 10 meters with stirred tank bioreactors often requiring less of a depth since the stifling can cause the bubbles to remain in the aqueous menstruum for a greater duration of time than those in a bubble column bioreactor. Regardless of the type of deep tank bioreactor, especially where using microbubbles that promote a stable dispersion of bubbles in the aqueous menstruum, mixing currents exist that not only assure the relatively uniform aqueous phase composition but also increase the contact time between the gas bubbles and the aqueous menstruum.

The processes of this invention are particularly attractive for deep tank bubble column bioreactors which are less expensive from cost and operating standpoints than other types of deep tank bioreactors. Where bubble column bioreactors are used, the depth of the aqueous fermentation menstruum is often at least about 15, say, between about 20 and 30, preferably between about 20 and 25, meters. The significant depths can be used in the bubble column bioreactors without undue risk of carbon monoxide inhibition as the substrate gas compositions provide a relatively low partial pressure of carbon monoxide even with these significant depths of aqueous fermentation menstruum.

Where more than one bioreactor is used in gas flow series, the initial bioreactor may be of any suitable configuration including, but not limited to, bubble column bioreactors; jet loop bioreactors; stirred tank bioreactors; trickle bed bioreactors; biofilm bioreactors; moving bed bioreactors; membrane bioreactors and static mixer bioreactors including, but not limited to, pipe bioreactors.

One broad aspect of the processes of this invention involve the use of at least two bioreactors, or bioreactor stages, in gas flow sequence where at least the last bioreactor stage has a substantially uniform liquid composition and a substantially non-uniform substrate composition. In this aspect of the processes of the invention, carbon monoxide is introduced to adjust the mole ratio of hydrogen to carbon monoxide and provide a hydrogen to carbon atom ratio in that bioreactor stage in the range of about 5.2:1 to 6.8. Preferably the mole ratio of hydrogen to carbon monoxide in the introduced carbon monoxide is less than about 5:1, say, in the range of about 2:1 to 4:1. While not wishing to be limited to theory, it is believed that the bioconversion of carbon monoxide which results in the formation of carbon dioxide, provides localized environments favoring the bioconversion of hydrogen to alcohol.

The carbon monoxide-containing gas may be derived from any suitable source including, but not limited to, gas from autothermal reforming and coke oven gas, provided that the hydrogen concentrations permit the sought hydrogen to carbon atom ratio to be achieved. The carbon monoxide-containing gas may be introduced into the aqueous menstruum and any suitable manner. For instance, if the bioreactor stage is a separate bioreactor vessel, the carbon monoxide-containing gas may be admixed with the gases passing to the bioreactor vessel. If the bioreactor stage is a zone with in a single bioreactor vessel, the carbon monoxide-containing gas may be introduced by sparging, liquid injection, or the like into that zone. Where using a bubble column bioreactor, the region at which the carbon monoxide-gas is introduced will be in an upper portion of the bioreactor which has a reduced static head. Thus, carbon monoxide-containing gas can have a relatively high carbon monoxide concentration without undue risk of carbon monoxide inhibition.

Another type of bioreactor suitable for the practice of this broad aspect of the invention uses a jet loop is at least the last bioreactor stage wherein the carbon monoxide-containing gas is used as a motive fluid for the gas lift.

Substrate Depleted Gas Phase

The depleted gas phase egressing from the aqueous fermentation menstruum will contain a small fraction of the hydrogen and carbon oxides introduced into the bioreactor assembly as the substrate gas. Inerts such as nitrogen and primarily methane will comprise a significant portion of the depleted gas phase. Thus the depleted gas phase has significant heating value when combusted or can be recycled, at least in part, to the unit operation used for producing the syngas. The carbon dioxide content of the depleted gas phase is sufficiently low that a recycle to the unit operation used for producing the syngas has a relatively immaterial effect on the syngas generation. The depleted gas phase may also contain sulfur-containing compounds, alcohol and the like volatilized from the aqueous fermentation menstruum. Table II provides typical concentrations of the major components in the substrate depleted gas phase from the bioreactor assembly using syngas from a steam reformer or autothermal reformer using oxygen from an air separation unit as the source of oxygen. The ratio of methane to hydrogen varies depending upon the amount of methane in the syngas, the conversion of hydrogen and whether a methane-containing carbon dioxide gas is used to adjust the electron to carbon ratio. Where an air fed autothermal reformer, nitrogen is often the major component of the substrate depleted gas, and sometimes is between about 60 and 90 volume percent of the substrate depleted gas. Due to the high nitrogen content, the substrate depleted gas has no value as a fuel. Accordingly, preferred operations using air fed autothermal reformers comprise using electron to carbon ratios that effect a hydrogen conversion to alcohol of at least about 90, preferably at least about 92, percent.

TABLE II

| Component | Usual, mole percent at 100 kPa absolute | Preferred, mole percent at 100 kPa absolute |
|---|---|---|
| Carbon monoxide | 0 to 5 | 0 to 1.5 |
| Hydrogen | 10 to 90 | 15 to 85 |
| Nitrogen | 0 to 10 | 0 to 2 |
| Methane | 5 to 90 | 5 to 80 |
| Carbon dioxide pp kPa | 2.5 to 30 or 40 kPa | 3.5 to 10 or 30 kPa |

(Mole percentages on an anhydrous basis, partial pressure include water vapor. The gas feed may contain other components)

Product Recovery:

The fermentation vessel may have added from time to time or continuously one or more streams of water, nutrients or adjuvants, and microorganisms. A portion of the aqueous menstruum is withdrawn from time to time or continuously from the bioreactor for product recovery. Usually, the withdrawal is made at a point at the upper portion of the aqueous menstruum in the vessel. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679, herein incorporated by reference in its entirety, shows an arrangement for a product recovery bioreactor that recovers an ethanol product from a bioreactor.

Drawings

A general understanding of the invention and its application may be facilitated by reference to the Figures. The Figures are not in limitation of the broad aspects of the invention.

FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering. FIG. 1 also omits ancillary unit operations. The process and operation of FIG. 1 will be described in the context of the recovery and production of ethanol. The process is readily adaptable to making other alcohols such as i-butanol, n-butanol, and n-propanol.

For purposes of discussion, natural gas will be used for providing the syngas for use in apparatus 100. It should be recognized that other carbonaceous sources can be used to provide syngas. The primary conversion process depicted is steam reforming although other syngas producing conversion unit operations can be used such as gasification, partial oxidation and autothermal reforming. Natural gas is supplied via line 102 and passed to pretreatment assembly 104. Pretreatment assembly 104 typically is adapted to remove sulfur compounds from the natural gas. In some instances, pretreatment assembly 104 is encompassed within a steam reforming unit operation.

The natural gas having its sulfur content reduced is passed via line 106 to heat exchanger 108 and then to steam reformer 110. Steam reformer 110 converts the hydrocarbons in the natural gas to a syngas containing hydrogen, carbon monoxide and carbon dioxide. Lower pressure operations of steam reformer 110 provide less methane breakthrough then at higher pressure operations. Accordingly, for purposes of discussion, a lower pressure steam reforming unit operation is used, and the syngas contains about 75 mole percent hydrogen, about 18 mole percent carbon monoxide, about 5.5 mole percent carbon dioxide, and about 1.5 mole percent methane on and anhydrous basis.

The steam reforming is highly endothermic and hotbox 112 is provided to supply heat for the steam reforming. Syngas exits steam reformer 110 via line 114 which directs the syngas to heat exchanger 108 to preheat the incoming natural gas to steam reformer 110. After passing through heat exchanger 108, carbon dioxide is supplied to the syngas in line 114 via line 116 in an amount sufficient to adjust the electron to carbon ratio of the syngas to about 6.3:1 and provide the sought amount of carbon dioxide in the depleted gas phase (off gas) from the bioreactor assembly. As shown, the combined syngas and carbon dioxide stream is subjected to treatment in syngas purification unit 118. The function of syngas purification unit 118 will depend upon the source of the syngas and carbon dioxide and serves to remove components that may be adverse to the microorganisms used for the anaerobic fermentation of the syngas to ethanol such as hydrogen cyanide, ethylene, and acetylene. Syngas purification unit 118 is optional, and thus using syngas from a steam reformer and carbon dioxide from an ethanol plant, it is not essential for the process depicted in the Figure.

The combined syngas and carbon dioxide stream (substrate gas) is passed from syngas purification unit 118 to bioreactor assembly 122 via line 120. For purposes of discussion, bioreactor assembly 122 comprises a plurality of deep tank bubble column bioreactors, one of which is shown in the drawing. Each deep tank bioreactor contains an aqueous fermentation menstruum having a depth of about 20 meters. The substrate gas is introduced at the bottom of the bioreactor in the form of finely dispersed microbubbles, e.g., using a slot eductor. The duration of the microbubbles in the bioreactor is sufficient to bioconvert at least 90 percent of the hydrogen and at least 98 percent of the carbon monoxide to ethanol.

Aqueous fermentation menstruum is continuously withdrawn from bioreactor assembly 122 via line 124. The withdrawn fluid is passed to a product recovery assembly generally designated by 126. Product recovery assembly 126 comprises a number of unit operations to remove solids, entrained gases and recover ethanol. Usually product recovery assembly 126 contains a distillation assembly to fractionate the withdrawn fluid into an ethanol product stream which is removed via line 128 and a water fraction which is removed via line 132. Centrifuges or other solid-liquid separation unit operations may be used to remove cells and other solid debris from the fluid prior to it being passed to the distillation assembly, or the fluid may be passed to the distillation assembly without the removal of solids with the solids being removed with the still bottoms. As shown, a solids-containing stream is removed from product recovery assembly 126 via line 134. The solids-containing stream may be directed to digesters to recover carbon and nutrient values. The withdrawn fluid will also typically include lower boiling components such as methane and hydrogen. These lower boiling components are shown as being removed from a product recovery assembly 126 via line 130. Due to the high efficiency of the processes of this invention, often the lower boiling components have a lower heating value and are sent to a flare for disposal.

Returning to a bioreactor assembly 122, make-up water to replenish aqueous menstruum removed for product recovery is provided via line 121. The make-up water may contain nutrients and other adjuvants for the anaerobic fermentation, and may also contain microorganisms for the bioconversion. Substrate depleted gas phase is emitted from the top of the aqueous fermentation menstruum in the bubble column bioreactor. The depleted gas phase contains about 3 volume percent carbon dioxide at substantially atmospheric pressure. The depleted gas phase is withdrawn from bioreactor assembly 122 via line 136. The depleted gas phase contains methane, hydrogen, carbon dioxide, and relatively little carbon monoxide and thus has value either as a supplement to the natural gas forced steam reforming or as a fuel for the steam reformer. As shown, the depleted gas phase in line 136 can be passed via line 138 to line 102 and then passed to pretreatment assembly 104. Since the depleted gas phase is derived from contact with the aqueous fermentation menstruum, it can contain sulfur compounds that were present in the aqueous menstruum as adjuvants for the microorganisms. The pretreatment assembly 104 serves to remove these sulfur compounds to provide a gas feed suitable for the catalytic steam reforming. In addition, or alternatively, depleted gas phase may be passed via line 140 to line 142 to supply natural gas to hotbox 112 for steam reformer 110. As shown, line 142 obtains the natural gas for hotbox 112 from line 102.

Carbon dioxide to provide the desired electron to carbon ratio for the substrate gas is obtained from an ethanol plant as described above. Other sources of carbon dioxide can be used. FIG. 1 illustrates that a carbonaceous material can be passed via line 144 to gasification unit 146. Gasification unit 146 serves to gasify the carbonaceous material, e.g., wood, to generate a gas containing carbon dioxide, carbon monoxide and hydrogen. Considerable flexibility exists in the operation of gasification unit 146 to provide a desired mole ratio of carbon dioxide to hydrogen such that when combined with the syngas from steam reformer 110, the substrate gas has the desired electron to carbon ratio and carbon dioxide content. Syngas exits gasification unit 146 via line 148. Not shown, but often desirable, is using the syngas which is at a high temperature as a source of heat for indirect heat exchange with the natural gas being provided to steam reformer 110. The syngas is directed to line 116 where it is combined with the syngas from steam reformer 110 in line 114. Syngas purification unit 118 is typically used. Combined gases can contain aromatic, ethylenic, acetylenic and hydrogen cyanide components that are preferably substantially removed prior to introducing the substrate gas into bioreactor assembly 122.

In another embodiment illustrated by FIG. 1, all feedstock in line 102 is passed via lines 142 and 144 to autothermal reformer 146. Line 147 provides the oxygen for the autothermal reforming. The oxygen may be sourced from an oxygen plant and thus be relatively high purity, from air or from oxygen enriched air produced by admixing air with purer forms of oxygen or by partial separation of nitrogen from air, e.g., by membrane separation or swing sorption. In this embodiment, the syngas may have a suitable electron to carbon atom ratio for introducing into bioreactor assembly 122 after suitable removal of deleterious components.

Figure 2:
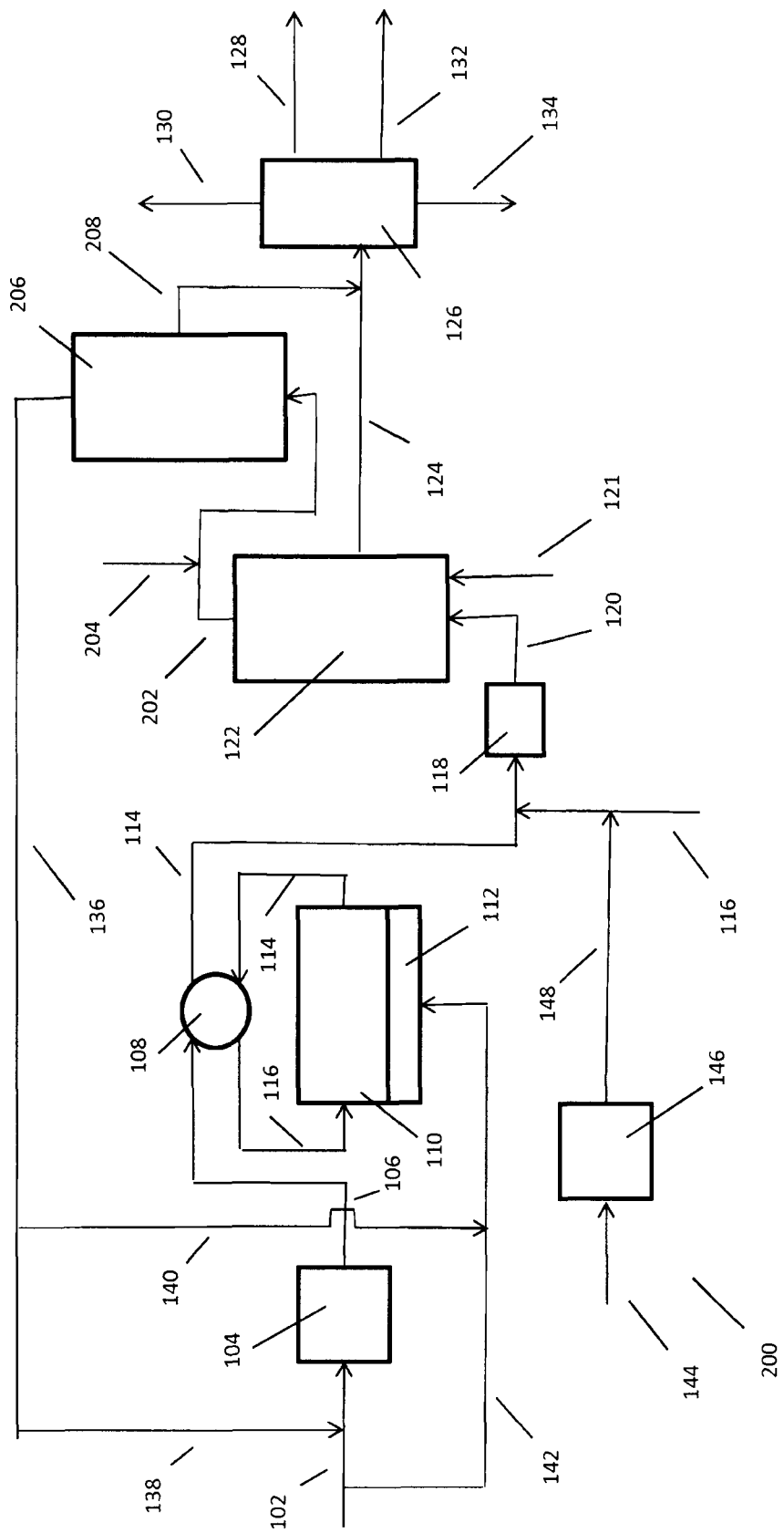
FIG. 2 is a schematic depiction of another apparatus suitable for practicing certain broad aspects of the processes of this invention.

FIG. 2 is a schematic depiction of apparatus 200 using two bioreactors in gas flow series suitable for obtaining high conversion efficiencies of hydrogen and carbon oxides to ethanol. The same numerals used in the description of the apparatus of FIG. 1 are used with respect to this FIG. 2 and the same description applies except as set forth below.

In bioreactor 122 a major portion of the hydrogen and virtually all, say, 90 or 95 percent or more, of the carbon monoxide are converted to ethanol, and an off gas containing hydrogen, carbon dioxide and relatively little carbon monoxide is generated. The off gas has an electron to carbon atom ratio greater than about 7:1. The off gas is withdrawn from bioreactor 122 via line 202 and passed to bioreactor 206 which is in gas flow sequence to bioreactor 122. Prior to the off gas entering bioreactor 206, carbon monoxide-containing gas supplied by line 204 is admixed with the off gas to provide a combined gas having a hydrogen to carbon atom ratio between about 5.5:1 to 6.5:1 and a hydrogen to carbon monoxide ratio of less than about 0.2:1. The carbon monoxide-containing gas may be a coal gas or other suitable gas, and may contain hydrogen and carbon dioxide such as syngas generated by gasification unit 146.

Bioreactor 206 converts hydrogen and carbon oxides to ethanol. For purposes of discussion, bioreactor 206 is a bubble column bioreactor with the combined off gas from bioreactor 122 and the carbon monoxide-containing gas being introduced in the form of finely divided bubbles. Aqueous menstruum containing ethanol is withdrawn from bioreactor 206 and passed via line 208 to line 124 for ethanol recovery. Depleted gas phase is withdrawn from the top of bioreactor 206 via line 136.

Figure 3:
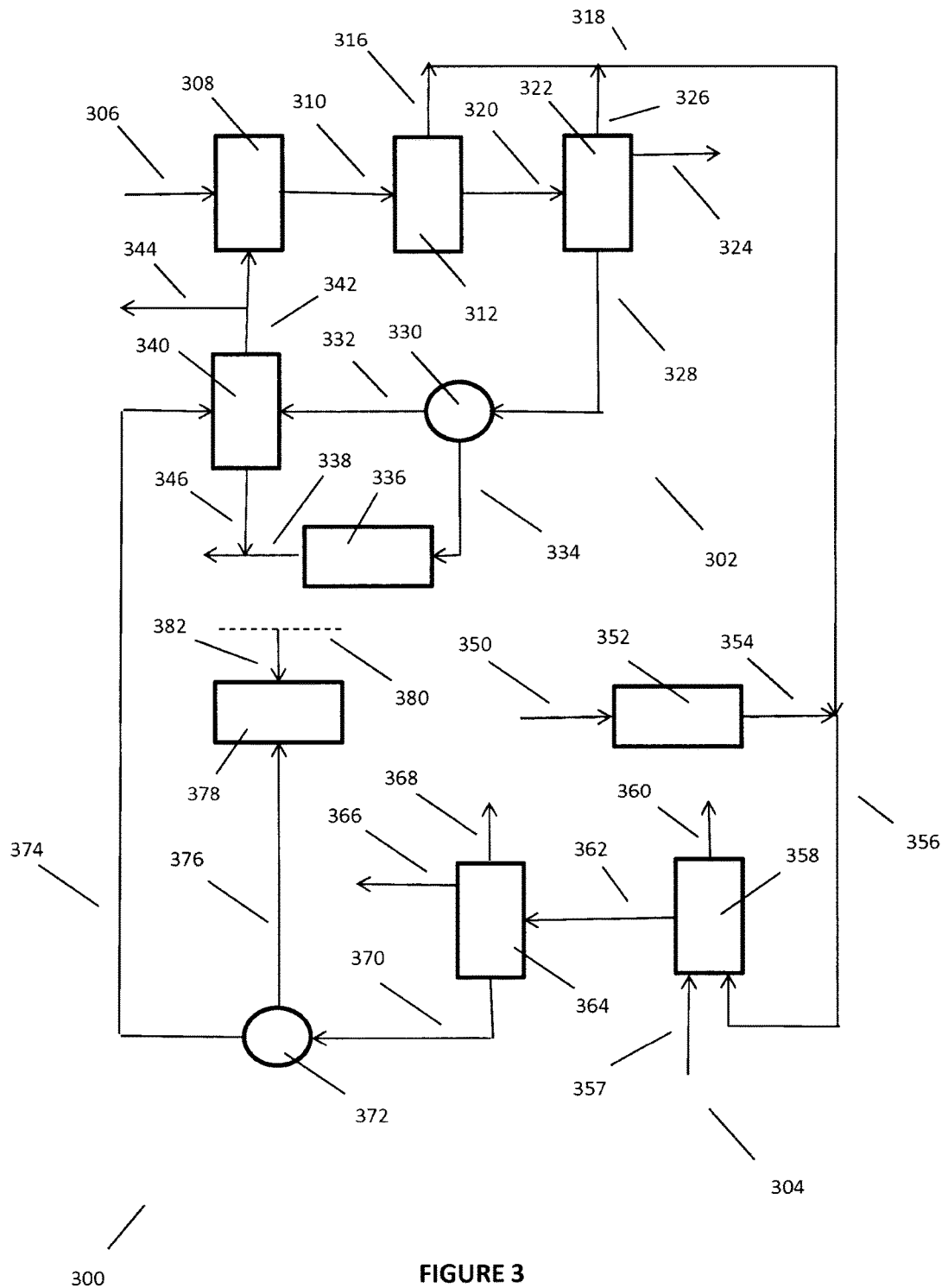
FIG. 3 is a schematic depiction of an integrated carbohydrate ethanol and anaerobic syngas bioconversion facility.

FIG. 3 is a schematic, simplified depiction of apparatus 300 containing an integrated corn ethanol facility 302 and syngas to ethanol facility 304. Corn and water are passed via line 306 to hydrolyzer 308 where the starches in the corn are broken down to sugars for fermentation. The hydrolyzate generated in hydrolyzer 308 is passed via line 310 to fermentation vessel 312 containing a fermentation broth using yeasts to convert the sugars to ethanol and carbon dioxide. Evolved carbon dioxide is passed via line 316 to carbon dioxide header 318. The fermentation broth is passed via line 320 into beer still 322. Beer still 322 separate by distillation and ethanol product which exits via line 324. A lights fraction exits there still 322 via line 326 which can, if desired, be passed to carbon dioxide header 318.

Beer still 322 as a solids and liquid-containing bottoms fraction, also known as the whole stillage. The whole stillage is withdrawn and passed via line 328 to centrifuge 330 to provide a thin stillage which exits via line 332 and wet distillers grains which exits via line 334. The wet distillers grains are passed to dryer 336 to provide dried distillers grains which are conveyed via line 338. Returning to the thin stillage in line 332, it is passed to the evaporator train 340. Evaporator train 340 has a plurality of evaporators and provides an overhead stream that is essentially water vapor which exits via line 342. The water vapor can be condensed and passed to hydrolyzer 308, as shown, or to fermentation vessel 312. If desired, a portion of the water may be withdrawn via line 344 for use, e.g., in syngas to ethanol facility 304. Evaporator train 340 also provides a concentrated sugar stream which exits via line 346 and can be combined with the dried distillers grains to provide dried distillers grains with solubles.

With respect to the syngas to ethanol facility 304, natural gas is provided via line 350 to steam reformer 352. Syngas from steam reformer 352 exits via line 354 buried is combined with carbon dioxide from carbon dioxide header 318. The combined gases are passed via line 356 to a bubble column bioreactor 358. The combined gases have an electron to carbon atom ratio of between about 5.5:1 to 6.5:1. A depleted gas phase is withdrawn via line 360 from bioreactor 358. The depleted gas phase may be used as fuel for the hotbox of steam reformer 352. From the aqueous menstruum in bioreactor 358 is withdrawn a stream for recovery of ethanol which is passed by line 362 to distillation assembly 364. Line 357 supplies make-up water to replenish aqueous menstruum removed for product recovery. The make-up water may contain nutrients and other adjuvants for the anaerobic fermentation, and may also contain microorganisms for the bioconversion. Distillation assembly 364 provides an ethanol product stream via line 366, a lights stream which exits via line 368 and a stream containing solids and water which exits via line 370.

The solids and water stream in line 370 is sent to centrifuge 372. Centrifuge 372 provides a clear water-containing stream that also contains dissolved salts. This clear water-containing stream is passed via line 374 to evaporator train 340 where water vapor is separated from salts containing concentrate.

A concentrated solids-containing fraction generated by centrifuge 372 is passed via line 376 to aerobic digester 378. Aerobic digester 378 is also servicing the corn ethanol facility 302. Wastewater from corn ethanol facility 302 is collected at various points through collector 380 and is passed via line 382 to aerobic digester 378. The solids provided by line 376 contain cell debris which contributes to the nitrogen source for the aerobic digester.

Figure 4:
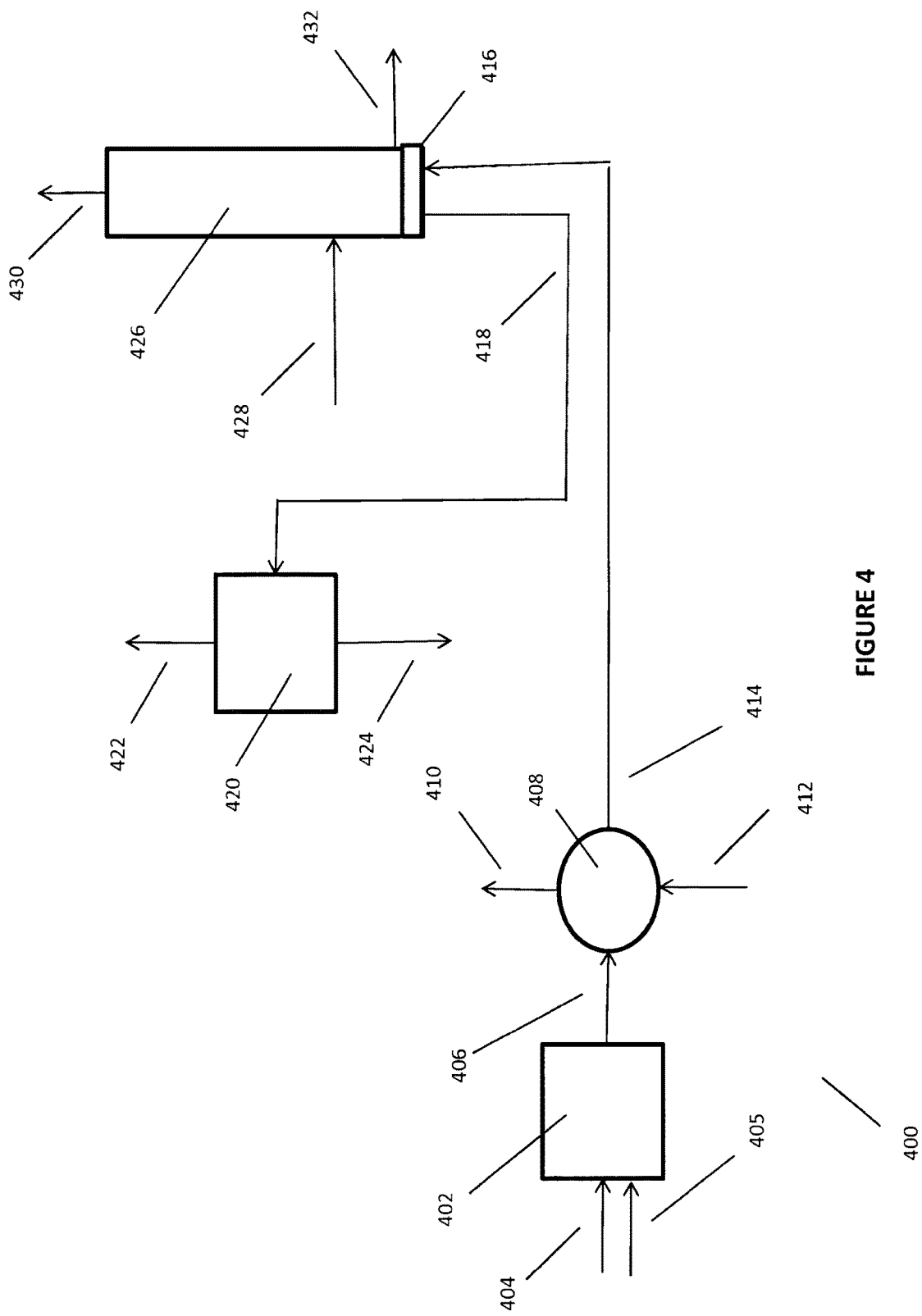
FIG. 4 is a schematic depiction of an integrated waste heat boiler from syngas generation and distillation reboiler for recovery of alcohol from aqueous menstruum.

FIG. 4 is a schematic depiction of an integration of unit operations generally designated by the number 400 to recover latent heat from syngas exiting a waste heat boiler for recovering heat from a reformer, and using the recovered heat in a distillation reboiler recovering alcohol. A reformer 402, which may be a steam reformer or autothermal reformer, is provided with hydrocarbonaceous feedstock via line 404. Where reformer 402 is an autothermal reformer, oxygen which may be pure oxygen, air or oxygen-enriched air is provided by line 405. Reformate exits via line 406 and is passed via line 406 to waste heat boiler 408 which generates steam at a pressure of about 950 kPa (absolute). The steam exits via line 410. Water is provided to waste heat boiler 408 via line 412. The cooled syngas contains about 33 volume percent water vapor and is at a temperature of about 128° C. and is passed via line 414 to distillation reboiler 416 which provides heat for distillation in distillation column 426. The syngas then passes to knock out vessel 420 via line 418 where condensate is removed. The syngas exiting knock out vessel 420 via line 422 contains about 12 volume percent water vapor and is at a temperature of about 104° C. Condensate exits knock out vessel 420 via line 424.

The syngas is used in an anaerobic fermentation to produce alcohol, which for ease of discussion will be designated as ethanol although other alcohols could be produced. FIG. 1 describes a suitable bioreactor assembly for the anaerobic bioconversion. Aqueous menstruum containing ethanol is passed to distillation column 426 via line 428. Ethanol exits distillation column 426 via line 430 and an aqueous bottoms stream is removed from distillation column 426 via line 432.

Figure 5:
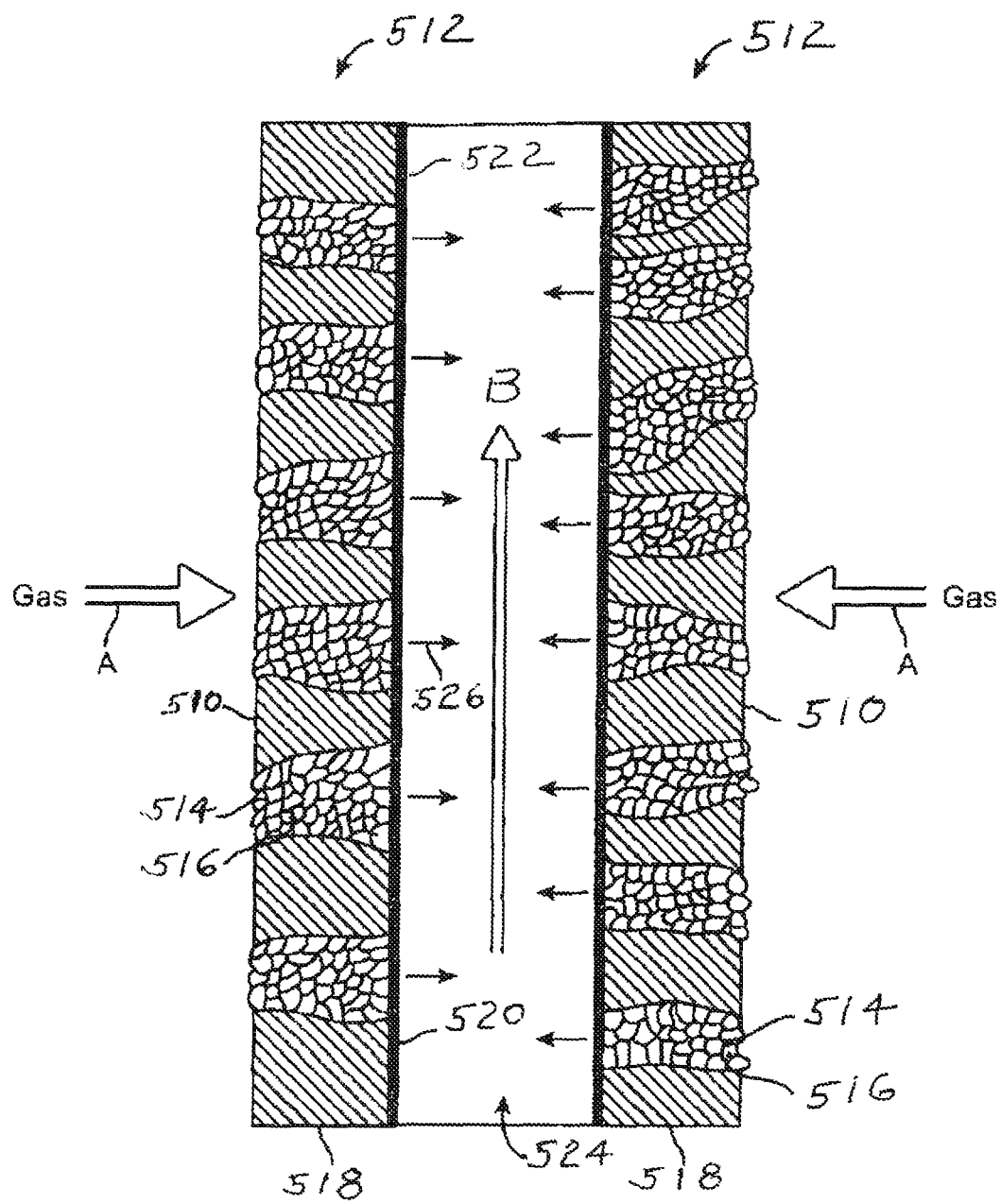
FIG. 5 is a schematic drawing showing a transverse cross-section of the asymmetric membrane of FIG. 1 made into a hollow fiber with the bio-layer on the outside and the hydration layer on the inside.

FIG. 5 shows a cross-section of an asymmetric membrane in a hollow fiber configuration, suitable for permeation of the fermentation liquid that provides the separation between the menstruum and the substrate. FIG. 5 shows more detail of the membrane configuration and interface in the operation of a representative bioreactor assembly and depicts a cross-section of a single hollow fiber membrane element with a substrate stream A flowing to the gas contacting side 510 of the asymmetric membrane 512. The substrate components directly contact the microorganisms 514 contained in biopores 516. The anaerobic acetogenic bacteria, *Clostridium ragsdaeli*, having all of the identifying characteristics of ATCC No. BAA-622, is maintained in the biopores and supplied with the fermentation liquid by permeation through the biolayer 518. The fermentation liquid circulates on the opposite side of the substrate A and permeates through a hydration layer formed as skin 520 on the inner surface of abio-layer 518. Direct contact of skin 520 with bio-layer 518 transfers the fermentation liquid to the bio-pores 516. The surfaces of bio-layer 518 that contact the microorganisms and gas stream serve as equilibrium partitioning across the asymmetric membrane to keep the menstruum and gas substrate separated from each other. The pores in skin 520 are much smaller than the width of the microorganisms retained in bio-pores 516 so that skin 520 occludes the inner end of bio-pores 516 and prevents the microorganisms from passing through skin 250 and to liquid contacting surface 522. As a result the microorganisms 514 preferentially stay within biopores 516 to gain metabolic energy by converting CO and $H_2/CO_2$ thereby growing and sustaining themselves within the biopores 516. A portion of liquid B is withdrawn and separated to recover the desired products from the fermentation liquid. Fermentation products pass out skin 520 in the direction of arrows 526.

Figure 6:
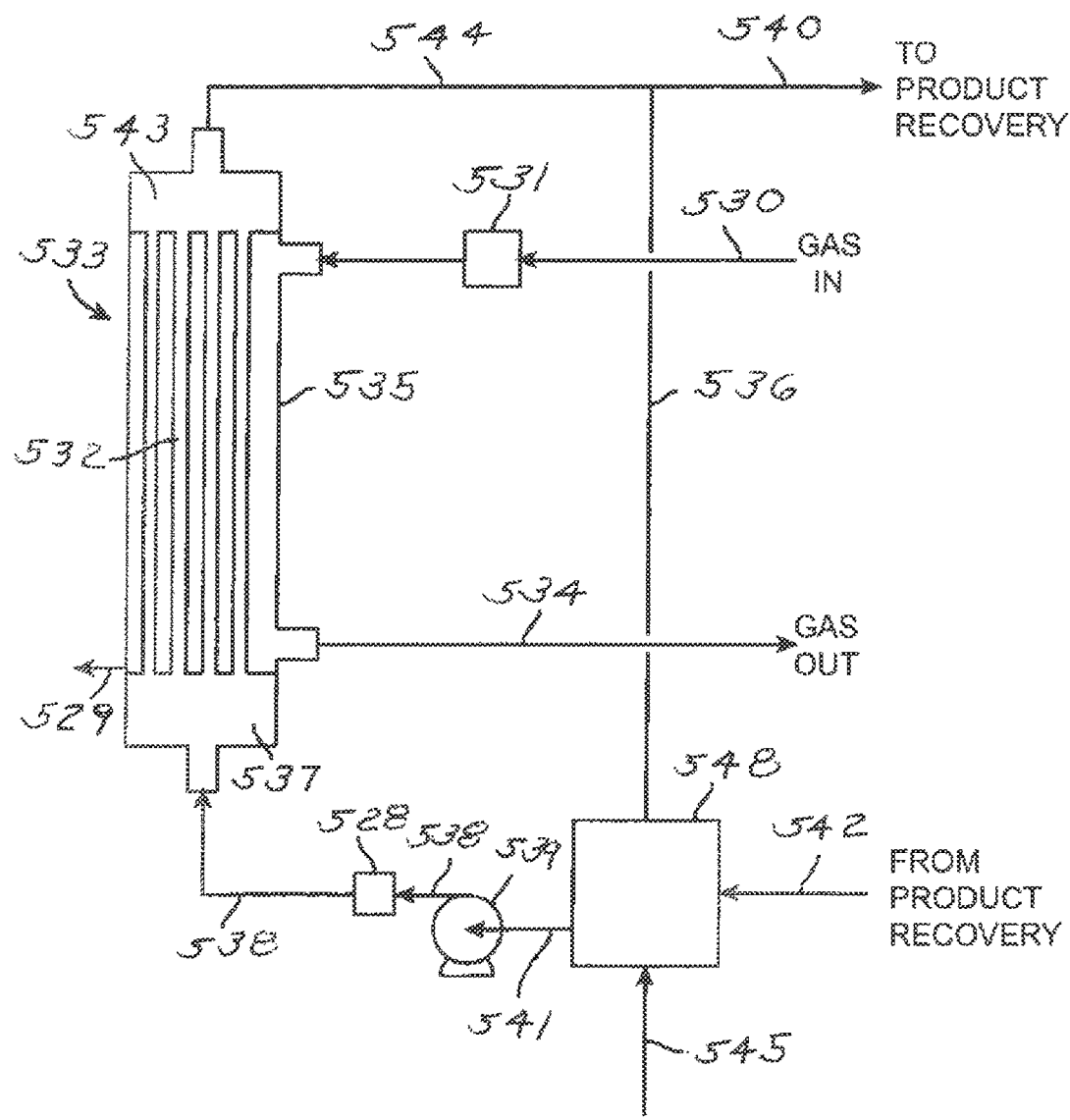
FIG. 6 is a schematic drawing of a bioreactor system showing gas and liquid circulation.

FIG. 6 illustrates a specific configuration of a bio-reactor assembly utilizing a membrane containing microorganisms. A gas supply conduit 530 delivers a substrate at a rate recorded by a flow meter 531 to a bioreactor 533. The bioreactor 533 includes a vessel 535 that surrounds the outside of the single module comprising membrane elements 532. Membrane elements 532 contain biopores to promote growth and maintenance of microorganisms within a biolayer on the outside of the membrane elements.

A feed gas distribution chamber 535 receives the feed gas stream and distributes it into direct contact with the outer surface of the membrane elements 532. The feed gas exits the vessel 535 via a line 534 such that a continuous addition of feed gas is established around the outer surface of membrane elements 532. The relative locations of the substrate feed line provides a downward direction of the bulk gas flow in the bioreactor 533.

Vessel 535 also contains a line 529 for draining liquid. Liquid may accumulate at the bottom of the vessel 535 for a variety of reasons such as condensation from moisture in the substrate, flushing or purging of the membrane elements or periodic cleaning operations.

Fermentation liquid enters bioreactor 533 via a conduit 538 under pressure supplied by a pump 539 and at rate recorded by a flow meter 528. A chamber 537 distributes fermentation liquid to the tubular membranes 532 via the bottom ends of the lumens. At the top end of bioreactor 533 a chamber 543 collects the fermentation liquid from the top of the lumens for withdrawal of the liquid via a conduit 544. The relative locations of chambers 537 and 543 establish upward flow of the liquid through bioreactor 533 so that there is countercurrent flow with respect to the bulk gas flow and the liquid flow.

A line 540 withdraws a net portion of the liquid from line 544 while the remainder of the liquid returns to the bioreactor 533 via a recirculation line 536 and mixing chamber 548, a line 541 and line 538. Line 540 carries the liquid to product recovery facilities that recover liquid products. Depending on the nature of the desired product, there are a number of technologies that can be used for product recovery. For example, distillation, dephlegmation, pervaporation and liquid-liquid extraction can be used for the recovery of ethanol and n-butanol, whereas electrodialysis and ion-exchange can be used for the recovery of acetate, butyrate, and other ionic products. In all cases the product recovery step removes the desirable product from stream 540, while leaving substantial amounts of water and residual nutrients in the treated stream as menstruum, part of which is returned to the bioreactor assembly via line 542 and mixing chamber 548.

Means for temperature and pH control for the liquid can be added anywhere along the re-circulating liquid loop, which consists of lines 538, 544, 536, and 541 as well as chambers 537, 343, and 548. A line 545 provides the nutrients needed to sustain the activity of the microorganisms to the re-circulating liquid loop chamber 548. Chamber 548 provides mixing of the nutrients and the other streams.

The flow rates of Streams 538 and 544, recirculated through the membrane unit, are selected so that there is no significant liquid boundary layer that impedes mass transfer near the liquid-facing side of the membrane. The superficial linear velocity of the liquid tangential to the membrane should be in the range of 0.01 to 20 cm/s, preferably 0.05 to 5 cm/s, and most preferably 0.2 to 1.0 cm/s.

Figure 7:
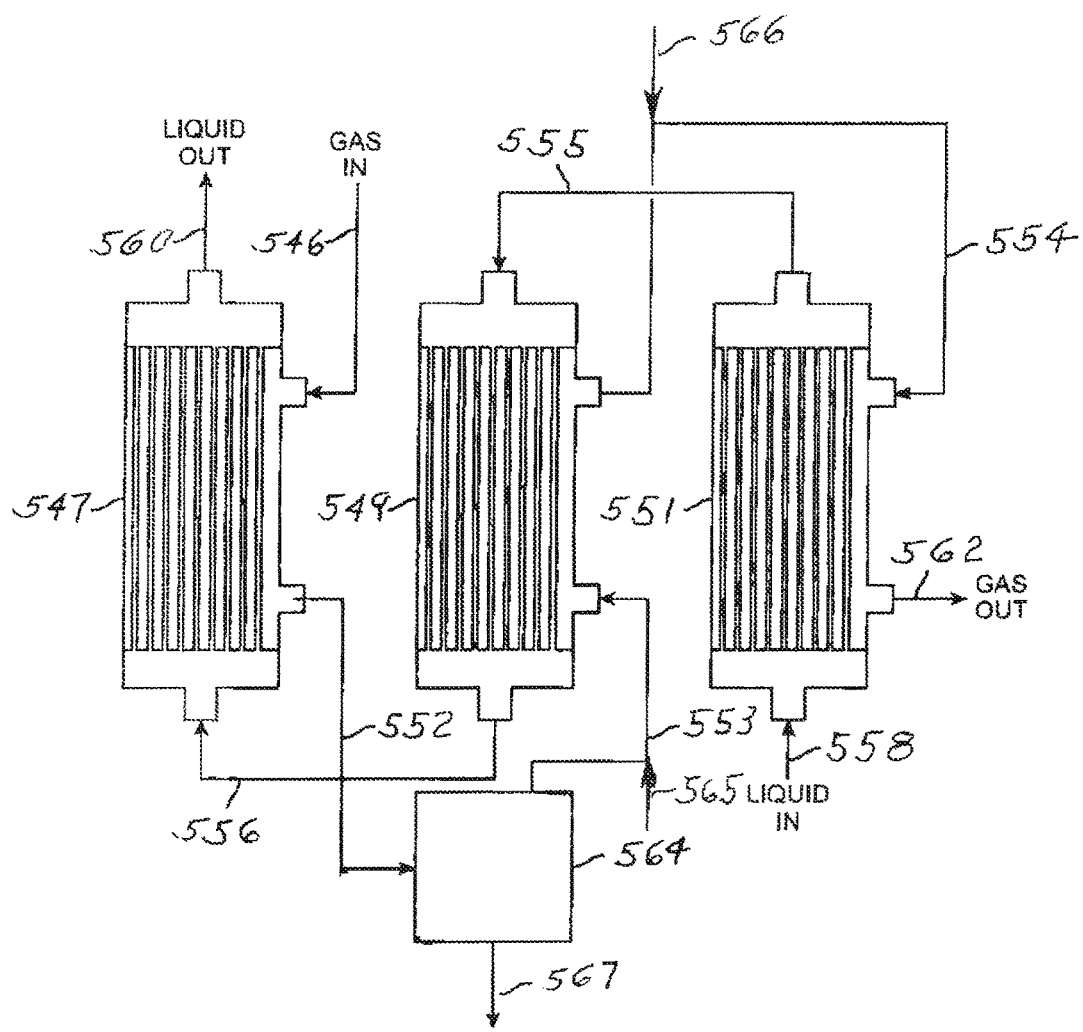
FIG. 7 is a schematic drawing showing a bioreactor system with multiple bioreactors arranged in series having intermediate carbon dioxide removal.

FIG. 7 depicts a system of multiple bioreactors in a bioreactor assembly. The entering substrate flows as a gas into bioreactor 547 via line 546 and serially through bioreactors 549 and 551 via lines 552, 553 and 554. At the same time liquid that contacts the microorganisms enters the system via line 558 and flows countercurrently, with respect to the gas flow, through bioreactors 547, 549 and 551 via lines 555 and 556. Liquid products are recovered from the liquid flowing out of line 560 and a gas stream is withdrawn from the system via line 562. Chamber 564 can be used for mixing or can serve a separation unit provides the gas stream of line 552 with a means for intermediate removal of gas stream components from the system via any suitable device or process such as a membrane or extraction step. Removed gas stream components flow out of line 567. Additional substrate of gas component can be added between bioreactors via lines 564 and 566. Interconnecting lines 555 and 556 also provide the function of establishing continuous communication through all of the lumens of the different bioreactors so that any combined collection and distribution chambers provide a continuous flow path.

The preamble to any claim in this invention is part of the entire claim and applies to interpreting the scope and coverage of each claim.

It is claimed:

1. A continuous process for the anaerobic bioconversion of a gas substrate comprising carbon monoxide, hydrogen and carbon dioxide in an aqueous menstruum containing microorganisms suitable for converting said substrate to an alcohol, that comprises:
   a. steam reforming hydrocarbonaceous feedstock to provide a syngas having an electron to carbon ratio greater than about 7:1, said steam reforming being performed in a steam reformer having at least one gas reforming section and at least one hotbox section;
   b. continuously introducing into a bioreactor assembly, said syngas and biogas, said biogas comprising at least about 20 or 25 mole percent carbon dioxide and at least about 40 mole percent methane, said biogas having an electron to carbon ratio not greater than about 0.1:1 to provide an overall gas substrate having an electron to carbon ratio in the range of about 5.2:1 to 6.8:1;
   c. continuously contacting said syngas and said biogas with said aqueous menstruum to bioconvert substrate gas to alcohol and providing an alcohol-containing menstruum and a substrate depleted gas phase, said contacting being in a bioreactor assembly containing said menstruum;
   d. continuously withdrawing substrate depleted gas phase from said aqueous menstruum, said depleted gas phase having a lower mole ratio of carbon dioxide to methane than that of the overall gas substrate;
   e. passing at least a portion of the depleted gas phase to the steam reformer of step (a); and
   f. continuously or intermittently withdrawing a portion of said menstruum for recovery of said alcohol, said withdrawal being sufficient to maintain the alcohol in said menstruum below a concentration that unduly adversely affects the microorganisms.

2. The process of claim 1 wherein at least a portion of the depleted gas phase is passed to the hotbox section of the steam reformer.

3. The process of claim 1 wherein at least a portion of the depleted gas phase is passed to the gas reforming section of the steam reformer.

4. The process of claim 3 wherein the depleted gas phase is subjected to a sulfur removal unit operation prior to being passed to the steam reforming section.

5. The process of claim 1 wherein the biogas comprises landfill gas.

6. The process of claim 1 wherein the biogas comprises anaerobic digester gas.

7. The process of claim 1 wherein the mole ratio of carbon dioxide to methane in the depleted gas phase is less than about 0.2:1.

8. A continuous process for the anaerobic bioconversion of a gas substrate comprising carbon monoxide, hydrogen and carbon dioxide in an aqueous menstruum containing microorganisms suitable for converting said substrate to an alcohol, the process comprising:
   a. continuously introducing into a bioreactor assembly containing aqueous menstruum a gas substrate having an electron to carbon ratio greater than 5.2:1;
   b. continuously contacting said syngas with said aqueous menstruum to bioconvert gas substrate to alcohol and providing an alcohol-containing menstruum and a substrate depleted gas phase;
   c. continuously withdrawing substrate depleted gas phase from said aqueous menstruum;
   d. passing at least an aliquot portion of the substrate depleted gas phase to a hot box section of a steam reformer; and
   e. continuously or intermittently withdrawing a portion of said menstruum for recovery of said alcohol, said withdrawal being sufficient to maintain the alcohol in said menstruum below a concentration that unduly adversely affects the microorganisms.

9. The process of claim 8 wherein the substrate depleted gas phase comprises less than about 50 mass percent of total fuel to the hot box.

* * * * *